US011058510B2

(12) United States Patent
Toossi et al.

(10) Patent No.: US 11,058,510 B2
(45) Date of Patent: Jul. 13, 2021

(54) SPINE-MOUNTED STEREOTACTIC SYSTEMS AND RELATED METHODS

(71) Applicants: The Governors of the University of Alberta, Edmonton (CA); Vanderbilt University, Nashville, TN (US)

(72) Inventors: Amirali Toossi, Edmonton (CA); Dirk Everaert, Edmonton (CA); Vivian Mushahwar, Edmonton (CA); Peter Konrad, Franklin, TN (US); Changqing Kao, Brentwood, TN (US)

(73) Assignees: The Governors of the University of Alberta, Alberta (CA); Vanderbilt University, Nashville, TN (US)

( * ) Notice: Subject to any disclaimer, the term of this patent is extended or adjusted under 35 U.S.C. 154(b) by 96 days.

(21) Appl. No.: 16/140,203

(22) Filed: Sep. 24, 2018

(65) Prior Publication Data
US 2019/0099235 A1    Apr. 4, 2019

Related U.S. Application Data

(60) Provisional application No. 62/562,197, filed on Sep. 22, 2017.

(51) Int. Cl.
*A61B 90/11* (2016.01)
*A61B 90/14* (2016.01)
*A61B 90/00* (2016.01)
*A61N 1/372* (2006.01)
*A61N 1/05* (2006.01)

(52) U.S. Cl.
CPC ............. *A61B 90/11* (2016.02); *A61B 90/14* (2016.02); *A61B 90/39* (2016.02);
(Continued)

(58) Field of Classification Search
CPC ......... A61B 90/10; A61B 90/11; A61B 90/14; A61B 90/16; A61B 90/37; A61B 90/39;
(Continued)

(56) References Cited

U.S. PATENT DOCUMENTS 8,574,232 B1 *  11/2013  Ross ................... A61F 5/042
                                                       606/57
2008/0306518 A1 * 12/2008  Cain .................. A61P 29/00
                                                       606/246

(Continued)

OTHER PUBLICATIONS

Federici, T. et al., "Surgical Technique for Spinal Cord Delivery of Therapies: Demonstration of Procedure in Gottingen Minipigs", Video Article, Journal of Visualized Experiments, Dec. 2012, pp. 1-5.

(Continued)

*Primary Examiner* — Katherine H Schwiker
*Assistant Examiner* — Alexis D Amechi
(74) *Attorney, Agent, or Firm* — Suiter Swantz pc llo

(57) ABSTRACT

A stereotactic system for positioning a device relative to a spine includes a first frame with an attached first pedicle screw, a second frame with an attached second pedicle screw, and a platform for mounting the device. The lower parts of the frames are horizontally spaced apart, and attachable to the spine by the pedicle screws. The platform is attached to the upper parts of the frames and supported by the frames above the spine. The platform is slidably attached to the upper parts of the frames to adjust a longitudinal position of the platform relative to the frames. The platform is pivotally attached to the upper parts of the frame to adjust a horizontal distance between the lower parts of the frames, while maintaining a constant orientation of the platform.

15 Claims, 16 Drawing Sheets

(52) U.S. Cl.
CPC ... *A61B 2090/374* (2016.02); *A61B 2090/378* (2016.02); *A61N 1/0551* (2013.01); *A61N 1/37205* (2013.01)

(58) Field of Classification Search
CPC ........ A61B 17/1671; A61B 2017/0256; A61B 17/1757; A61B 2090/506; A61B 90/50; A61B 8/4209; A61B 17/645; A61B 2017/3413; A61B 2090/374; A61B 2090/373; A61B 2090/378; A61B 17/3403; A61B 17/3472; A61B 90/13; A61B 90/17
See application file for complete search history.

(56) References Cited

U.S. PATENT DOCUMENTS

| | | | |
|---|---|---|---|
| 2010/0030184 A1* | 2/2010 | Boulis | A61B 17/3472 604/500 |
| 2019/0175214 A1* | 6/2019 | Wood | A61B 17/3403 |

OTHER PUBLICATIONS

Riley, Jonathan P. et al., "Platform and Cannula Design Improvements for Spinal Cord Therapeutics Delivery", Neurosurgery, vol. 69, Dec. 2011, pp. 147-154.

Riley, Jonathan et al., "Intraspinal Stem Cell Transplantation in Amyotrophic Lateral Sclerosis: A Phase I Safety Trial, Technical Note, and Lumbar Safety Outcomes", Neurosurgery, vol. 71, No. 2, Aug. 2012, pp. 405-416.

Riley, Jonathan et al., "Targeted Spinal Cord Therapeutics Delivery: Stabilized Platform and Microelectrode Recording Guidance Validation", Stereotactic and Functional Neurosurgery, Dec. 12, 2007, 86:67-74, DOI: 10.1159/000112426.

Busscher, Iris et al., "Comparative anatomical dimensions of the complete human and porcine spine", Eur Spine J, 2010, 19:1104-1114, DOI: 10.1007/s00586-010-1326-9.

Grahn, Peter J. et al., "MRI-guided sterotactic system for delivery of intraspinal microstimulation", Spine, Jul. 1, 2016, 41(13): E806-E813, DOI: 10/1097/BRS.0000000000001397.

* cited by examiner

MRI

Ultrasound

SPINE-MOUNTED STEREOTACTIC SYSTEMS AND RELATED METHODS

FIELD OF THE INVENTION

The present invention relates to a stereotactic system that assists with precise positioning of a device relative to the spine, as may be needed in intraspinal therapeutic procedures such as intraspinal cell injection or intraspinal microstimulation.

BACKGROUND TO THE INVENTION

In the treatment of neurological injury or disease, one intraspinal therapeutic procedure that is developing towards clinical use on humans is intraspinal cellular injection in which cells (e.g., stem cells) are injected into the spinal cord using a cannula. Another such intraspinal therapeutic procedure is intraspinal microstimulation (ISMS) in which small electrodes are implanted in the spinal cord and energized. Successful implementation of these intraspinal therapeutic procedures requires the ability to precisely position a device (e.g., the cannula or the electrodes) relative to the spine. For example, for ISMS, the spatial targeting error for the electrodes should be less than 0.5 mm.

For ISMS, one approach is to use solid-based electrode arrays mounted in an apparatus for en masse insertion of the electrodes. This approach has been abandoned due to the extensive damage to the spinal cord the solid-based arrays have caused. Thus, most approaches to date have involved the insertion of individual electrodes in spinal cords by hand, which is less damaging and better tolerated by the spinal cord. However, the procedure is slow, and can be inconsistent if applied by an inadequately trained surgeon. Because adequate training requires extensive time and effort, clinical translation of the ISMS approach may be limited to very few centers in the world.

Stereotactic systems to assist with placement of devices in spinal surgery are known in the art. They can be categorized into two groups based on whether they are mounted on the surgical table, or on the spine of the patient. One drawback associated with stereotactic systems that are mounted on the surgical table is the risk of damaging the spinal cord because of relative displacements between the surgical table and the spinal cord. These relative displacements could result from physiological movements (e.g., breathing and vascular pulsations) and externally induced motions (e.g., adjustments in patient position or movements of the limbs). This is especially critical for procedures such as ISMS where electrical stimulation through the implant produces movements in the limbs that can change the length of the spinal cord and generate displacements in the spinal column and spinal cord. Stereotactic systems mounted on the spine of the patient alleviate this drawback.

Two spine-mounted stereotactic systems have been reported in the literature. The first, called the spinal derrick, was developed at Emory University for intraspinal stem cell delivery and has been tested clinically (see references [1] and [2] listed below). The system involves the fixation of four percutaneous posts into the spine, which posts are used to mount two rails. A gondola, hosting an injector, slides on the rails. A micromanipulator system is then assembled on top of the gondola. The system is relative bulky and may not provide adequate fixation of the spinal column. As the fixation points span several segments, a large surgical exposure may be needed and movement can occur between the mounting vertebrae, which may be associated with a risk of damaging the spinal cord during cellular injections. In most of the preclinical and clinical studies using this system, estimation of the implant trajectory within the spinal cord was based on dorsal anatomical landmarks, micromanipulator coordinates and magnetic resonance imaging (MRI) acquired prior to the surgery. The targeting accuracy of this implant delivery system was not systematically reported. However, the reported injection targets in human spinal cords are in the ventral horns of the gray matter at depths ranging from 3-5 mm from the dorsal surface (see reference [3] listed below) and unlike ISMS, may not require submillimeter targeting accuracies. In an earlier study (see reference [4] listed below), microelectrode recording and stimulation was used with the spinal derrick to identify the boundary between the gray and white matter in the spinal cord. This targeting method however, was later abandoned as it required multiple passes and electrode penetrations at each injection site. More recently, a prototype of an MR-compatible spinal derrick was used for MRI guided insertion of injection needles through the interlaminar space (see reference [5] listed below).

The second patient-mounted stereotactic system was developed at the Mayo clinic for ISMS in pigs (see reference [6] listed below). The system anchors to the spine through eight MR-compatible pedicle screws spanning four vertebral levels. The system contains a microdrive on a "stereotaxic platform" that is mounted on a "spine platform" secured with rods to the pedicle screws. The platform is relatively large, requiring eight pedicle screws and a relatively large surgical exposure. The frame is also not non-adaptive to different patients. A different frame is needed for each patient, which limits the wide-spread utility of the system. Moreover, the frame is relatively heavy, which may be associated with a risk of damaging the vertebrae on which it is mounted. MRIs are obtained following the laminectomy and pedicle screw placement, using a custom MR coil and MM markers. The coil and markers are then removed and the micromanipulator setup is mounted on the pedicle screws. The acquired MR images guide the coordinates on the micromanipulator system for targeting within the spinal cord. The reported targeting accuracy of this system in a bench setup was 1.09±0.2 mm (mean±standard deviation). Methods that only use MR images that are collected prior to the insertion of the electrodes lack the ability to provide guidance and feedback during or after insertion.

SUMMARY OF THE INVENTION

There remains a need in the art for a stereotactic system for precise positioning of a device (e.g., an injection cannula or an electrode) relative to the spine, as may be needed in an intraspinal spinal therapeutic procedure.

In one aspect, the present invention includes a stereotactic system for positioning a device relative to a spine extending craniocaudally in a horizontally extending longitudinal direction. The system includes:

(a) a first frame comprising a lower part and an upper part, and at least one first pedicle screw attached to the first frame for fixedly attaching the lower part of the first frame to the spine;

(b) a second frame comprising a lower part and an upper part, and at least one second pedicle screw attached to the second frame for fixedly attaching the lower part of the second frame to the spine, wherein the lower part of the second frame is horizontally spaced apart from the lower part of the first frame; and (c) a platform for mounting the device, wherein:
  (i) the platform is attached to the upper part of the first frame and the upper part of the second frame so as to be supported by the frames above the spine when the frames are fixedly attached by the pedicle screws to the spine;
  (ii) the platform is slidably attached to the upper part of the first frame and the upper part of the second frame to allow for selective adjustment of a longitudinal position of the platform relative to the frame; and
  (iii) the platform is pivotally attached to the upper part of the first frame and to the upper part of the second frame, to allow for selective adjustment of a horizontal distance between the lower part of the first frame and the lower part of the second frame, while maintaining a constant orientation of the platform.

In an embodiment of the system, the upper part and the lower part of the first frame intersect a common horizontally extending transverse plane substantially perpendicular to the longitudinal direction. The upper part and the lower part of the first frame may form part of a vertically extending closed loop.

In an embodiment of the system, the upper part and the lower part of the first frame are longitudinally spaced apart, such that the upper part and the lower part do not intersect a common horizontally extending transverse plane substantially perpendicular to the longitudinal direction.

In an embodiment of the system, the upper part and the lower part of the first frame are formed by at least one elongate rod, which may be a metallic surgical spine rod.

In an embodiment of the system, the system further includes a least one length-adjustable brace member attached to the first frame and the second frame.

In an embodiment of the system, each of the pedicle screws may be slidably attached to one the frames to allow for selective adjustment of a horizontal position of the pedicle screw relative to the one of the frames.

In an embodiment of the system, each of the pedicle screws may be pivotally attached to one of the frames to allow for selective adjustment of an orientation of the pedicle screw relative to the one of the frames.

In an embodiment of the system, the system includes a micromanipulator for holding the device, wherein the micromanipulator is mounted on the platform. The micromanipulator may be moveably mounted on the platform for moving relative to the platform in up to six degrees of freedom.

In an embodiment of the system, the system includes an ultrasound probe for use in dynamic, real-time imaging of the device. The ultrasound probe may be attached to the frame. The ultrasound probe may be pivotally attached to the frame to allow for selective adjustment of an orientation of the ultrasound probe relative to the frame about a horizontally extending axis. Alternatively, the ultrasound probe may be handheld.

In another aspect, the present invention may include a method of using a system of the present invention as described herein.

The system of the present invention may be constructed to be relatively light in weight. The system may be constructed in a modular manner, in which embodiments of the constituent components of the frame and the platform may be detached from each other and substituted with other embodiments of the constituent components, so that the system may be adapted to different patients having different anatomies, or to define different surgical windows for different therapeutic procedures. The system may allow for precise positioning of the device, and precise control of the insertion angle and depth of the device in the spine. The system may limit or avoid unintended movement of the device relative to the spine. The system may be convenient to set up for use, and compatible for use with standard surgical tools.

BRIEF DESCRIPTION OF THE DRAWINGS

In the drawings shown in the specification, like elements may be assigned like reference numerals. The drawings are not necessarily to scale, with the emphasis instead placed upon the principles of the present invention. Additionally, each of the embodiments depicted are but one of a number of possible arrangements utilizing the fundamental concepts of the present invention.

DETAILED DESCRIPTION OF PREFERRED EMBODIMENT

Figure 1:
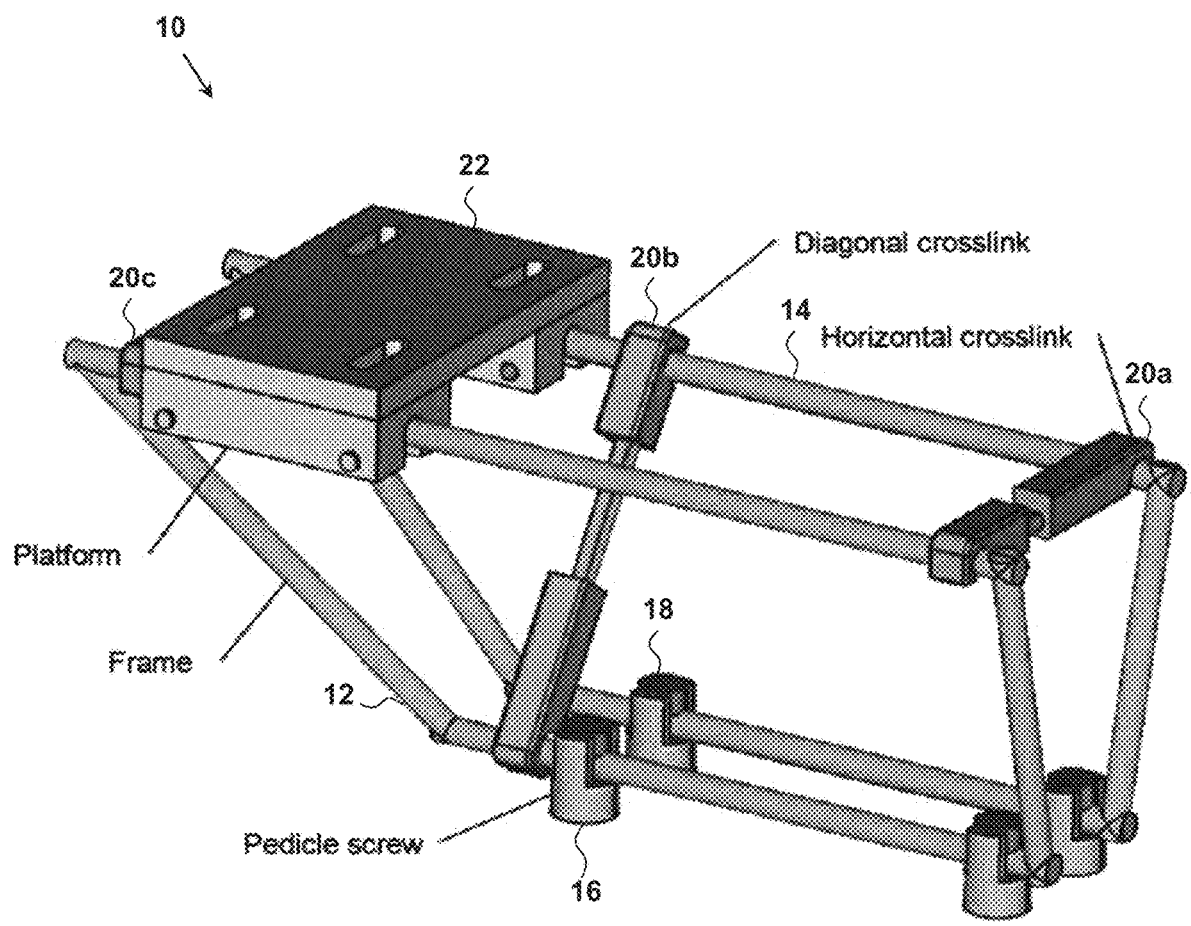
FIG. 1 is perspective view of an embodiment of a system of the present invention.
Figure 2:
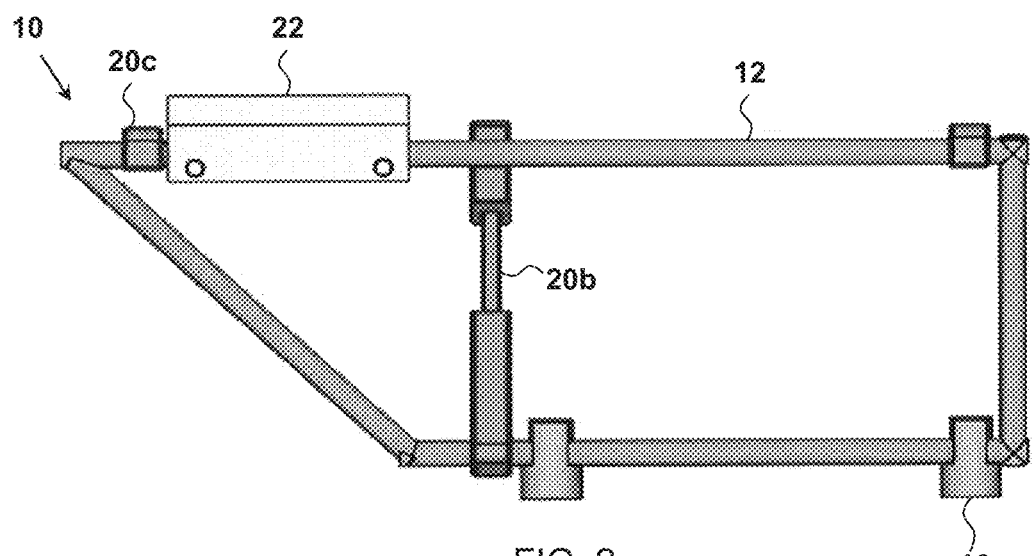
FIG. 2 is side view of the system shown in FIG. 1.
Figure 3:
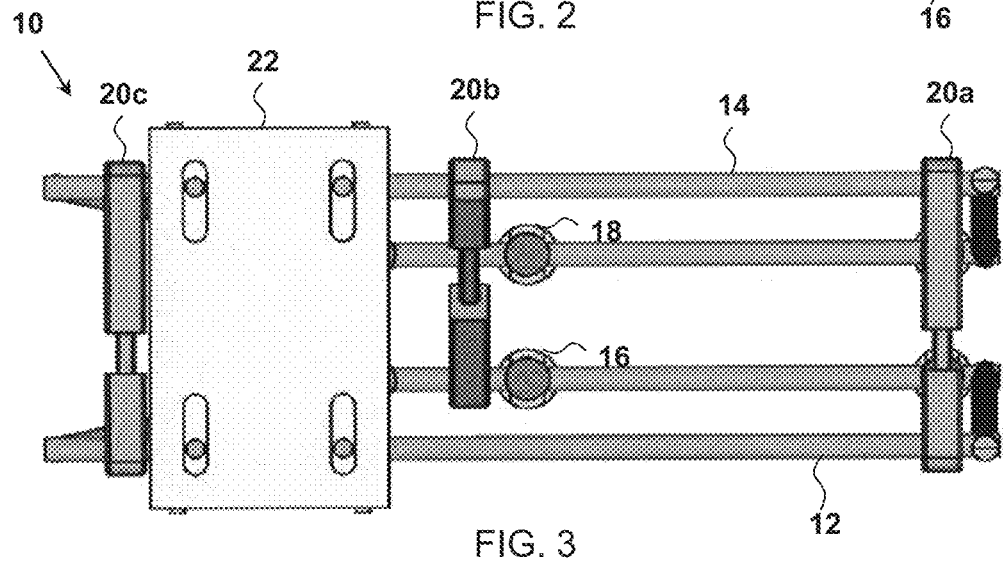
FIG. 3 is top view of the system shown in FIG. 1.

Definitions. The present invention includes a stereotactic system for positioning a device relative to a spine. Any term or expression not expressly defined herein shall have its commonly accepted definition understood by a person skilled in the art. As used herein, the following terms have the following meanings. As used herein, "longitudinal" refers to the horizontally extending direction substantially aligned with a sagittal plane of the spine (i.e., parallel to the length of the spine from the cranial end to the caudal end). As used herein, "transverse" refers to the horizontally extending direction substantially perpendicular to the longitudinal direction. As used herein, "attached", "connected" in describing the relationship between two parts includes the case where the two parts directly engage each other without any intermediate part, as well as the case where the two parts engage each other indirectly via one or more intermediate parts.

Overview. As shown in FIGS. 1 to 4, an embodiment of the system (10) of the present invention generally includes a first frame (12), a second frame (14), at least one first pedicle screw (16) associated with the first frame (12), at least one second pedicle screw (18) associated with the second frame (14), at least one length-adjustable brace member (20), and a platform (22). These components of the system, as well as additional components are described in greater detail below.

Frames and length-adjustable brace member(s). A purpose of the first and second frames (12, 14) is to support the platform (22) above the spine when the frames (12, 14) are attached to the spine. Each of the frames (12, 14) includes an upper part and a lower part. A purpose of the upper part of each frame is attachment to the platform (22), as is further discussed below. A purpose of the lower part of each frame is to be fixedly attached by one or more pedicle screws (16, 18) to the spine, as is further discussed below. The lower parts of the first and second frame are horizontally spaced apart from each other for attachment to different parts of the spine. A purpose of the length-adjustable brace member(s) (20) is to stabilize the first and second frames (12, 14) relative to each other.

In embodiments, each of the frames (12, 14) may be formed by one or more commercially surgical spine rods (e.g., 5.5 mm diameter rods, from Medtronic PLC, Dublin, Ireland). As such, the rods are compatible with commercially available surgical spine instrumentation components, such as the pedicle screws and rod crosslinks.

As shown in FIGS. 1 to 4, an embodiment of the frame (12, 14) is formed by four elongate surgical spine rods joined together, end to end, to form a quadrilateral-shaped, vertically-extending, closed loop. The top-most rod extends horizontally, and forms the upper part of the frame (12, 14). The bottom-most rod extends horizontally, parallel to and directly below the top most rod, and forms the lower part of the frame (12, 14). The two other rods extend vertically between the top-most and bottom-most rod.

In other embodiments (not shown), the closed loop formed by the surgical spine rods may be rectangular in shape, with the top-most rod and the bottom-most rod having the same length. In such embodiments, the length of the rectangular loop is determined by the size of the "working window" required for a micromanipulator, on the upper part of the loops. It will be appreciated, however, that a longer "working window" at the top also requires a longer surgical opening and exposure of bone.

Preferably, the system should fit within the standard surgical opening, without needing a larger opening to accommodate the micromanipulator working window. Therefore, in embodiments, such as shown in FIGS. 1 to 4, the longitudinal length of the frame (12, 14) at the bottom may be made shorter than the longitudinal length of the frame (12, 14) at the top. This configuration requires less exposure of the spine in the craniocaudal direction, while providing a sufficiently large working window at the top of the frames (12, 14). As an illustrative example, the longitudinal length of the frame (12, 14) at the bottom and top of the frame (12, 14) may be about 11 cm and 17 cm, respectively, and the vertical height of the frame (12, 14) may be about 7 cm.

As shown in FIGS. 1 to 4, the frames (12, 14) are stabilized by three length-adjustable brace members (20a, 20b, 20c), each of which is formed by an extendible crosslinks (e.g., crosslinks from Medtronic PLC, Dublin, Ireland) that are attached to and extend transversely between the frames (12, 14). The first crosslink (20a) attaches to the top-most rod of each of the frames (12, 14). The second crosslink (20b) attaches to the bottom-most rod of one of the frames (12, 14), and to the top-most rod of the other frame. The third crosslink (20c) attaches to the top-most rod of each of the frames (12, 14) at an opposite end of the frames (12, 14). As a non-limiting illustrative example, the fully extended length of the first and third crosslinks (20a, 20c) may be about 5.5 cm, and the fully extended length of the second crosslink (20b) may be about 7.5 cm. In other embodiments (not shown), the crosslinks may attach to different parts of the frames (12, 14).

Figure 5:
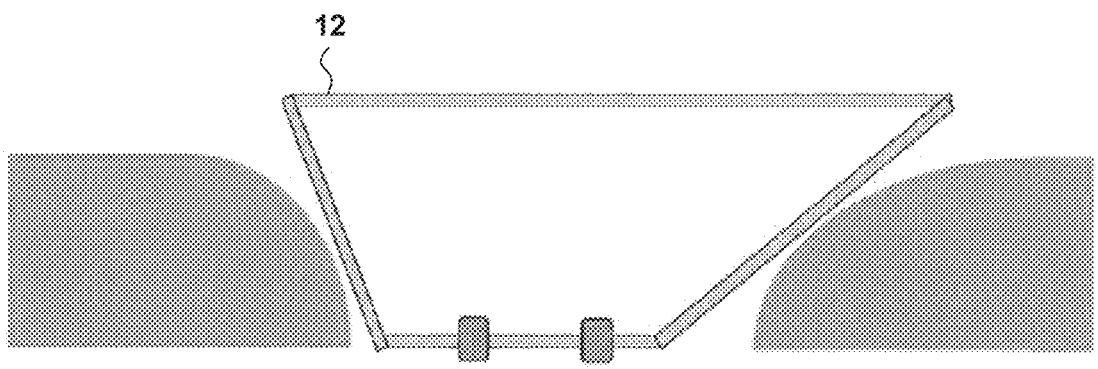
FIG. 5 is a side view of an embodiment of a short frame and attached pedicle screws of another embodiment of a system of the present invention, when disposed between paraspinal tissue.
Figure 6:
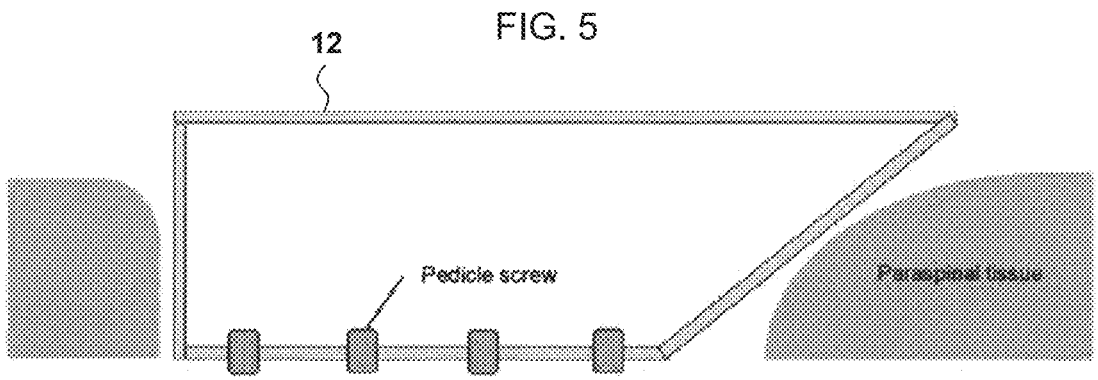
FIG. 6 is a side view of an embodiment of a long frame and attached pedicle screws of another embodiment of a system of the present invention, when disposed between paraspinal tissue.
Figure 7:
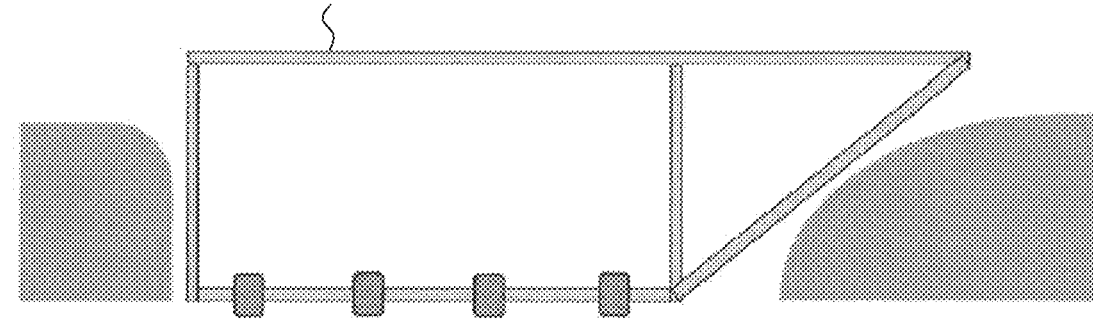
FIG. 7 is a side view of an embodiment of a long frame with a vertical stiffening rod and attached pedicle screws of another embodiment of a system of the present invention, when disposed between paraspinal tissue.
Figure 8:
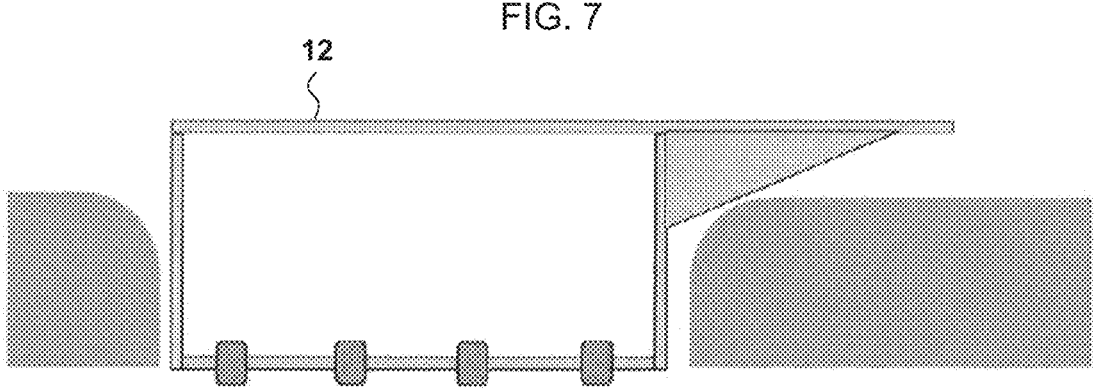
FIG. 8 is a side view of an embodiment of a long frame with a stiffening gusset plate and attached pedicle screws of another embodiment of a system of the present invention, when disposed between paraspinal tissue.

As shown in FIGS. 5 to 8, different embodiments of the frame (12, 14) may have different morphologies (size, shape, and construction). (The first and seconds frames (12, 14) may have the same or different morphologies in terms of size, shape, and construction.) For example, a kit of frames (12, 14) of different morphologies can be supplied with platforms (22) of different morphologies for adaptation to patients of different morphology and to different spinal therapeutic procedures requiring different surgical exposures of the spine or target windows of the device. FIGS. 5 and 6 show embodiments of a frame (12, 14) having a bottom-most rod that is relatively shorter and longer, respectively, in the longitudinal direction for fixation on two and four vertebrae, respectively. FIG. 7 shows an embodiment of a frame (12, 14) similar to that of FIG. 6, having a fifth rod extending vertically between and attached to the bottom-most and top-most rods to provide additional stiffness to the frame. FIG. 8 shows another embodiment of a frame (12, 14) similar to that of FIG. 7, except that the obliquely angled vertically extending rod has been replaced with a gusset plate to provide additional stiffness to the frame.

Figure 9:
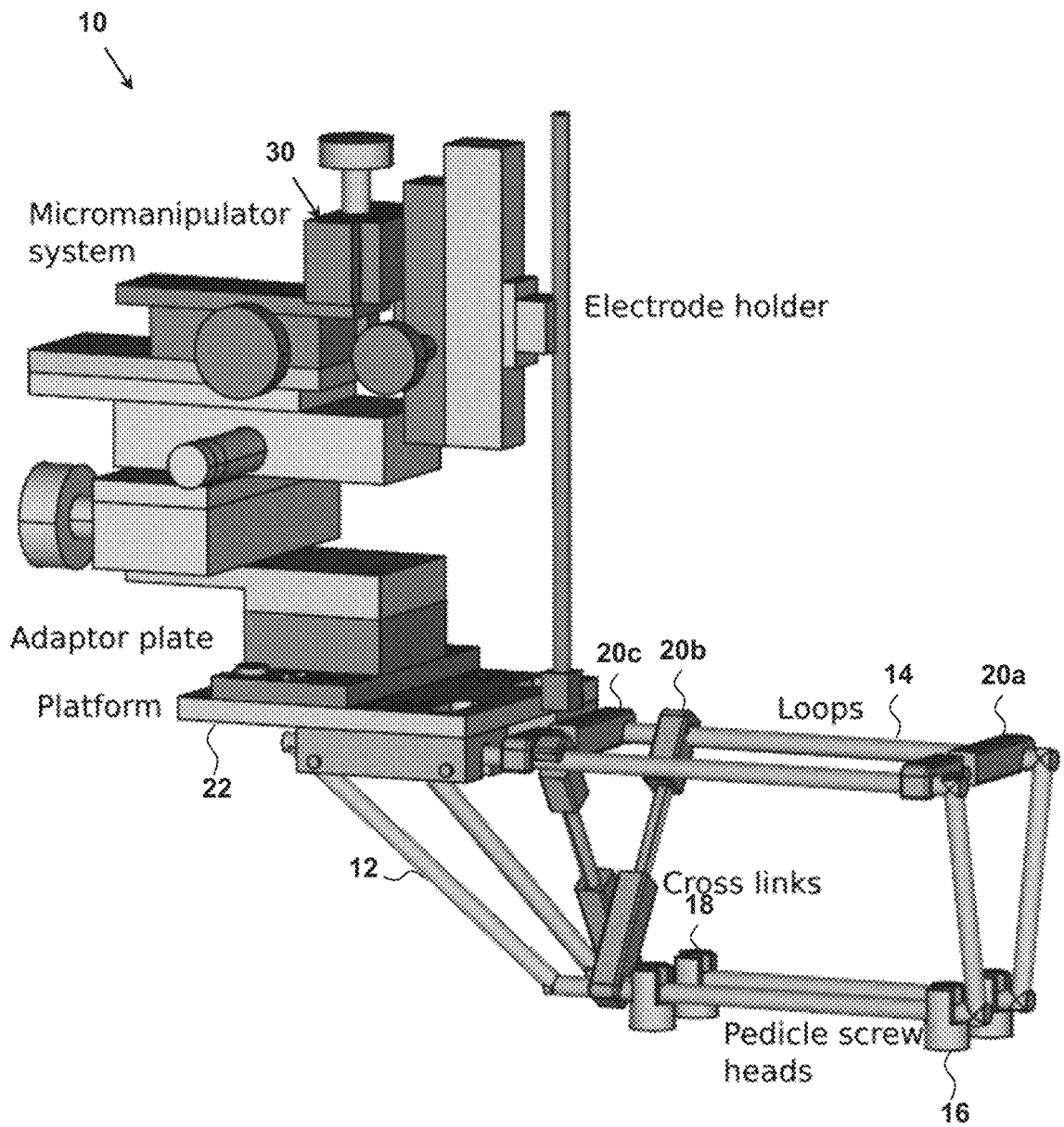
FIG. 9 is a perspective view of another embodiment of a system of the present invention in combination with a micromanipulator system holding an electrode mounted thereon.

As shown in FIG. 9, another embodiment of the frame is similar to the embodiment shown in FIGS. 1 to 4. However, a third crosslink (20c) has been repositioned.

Figure 10:
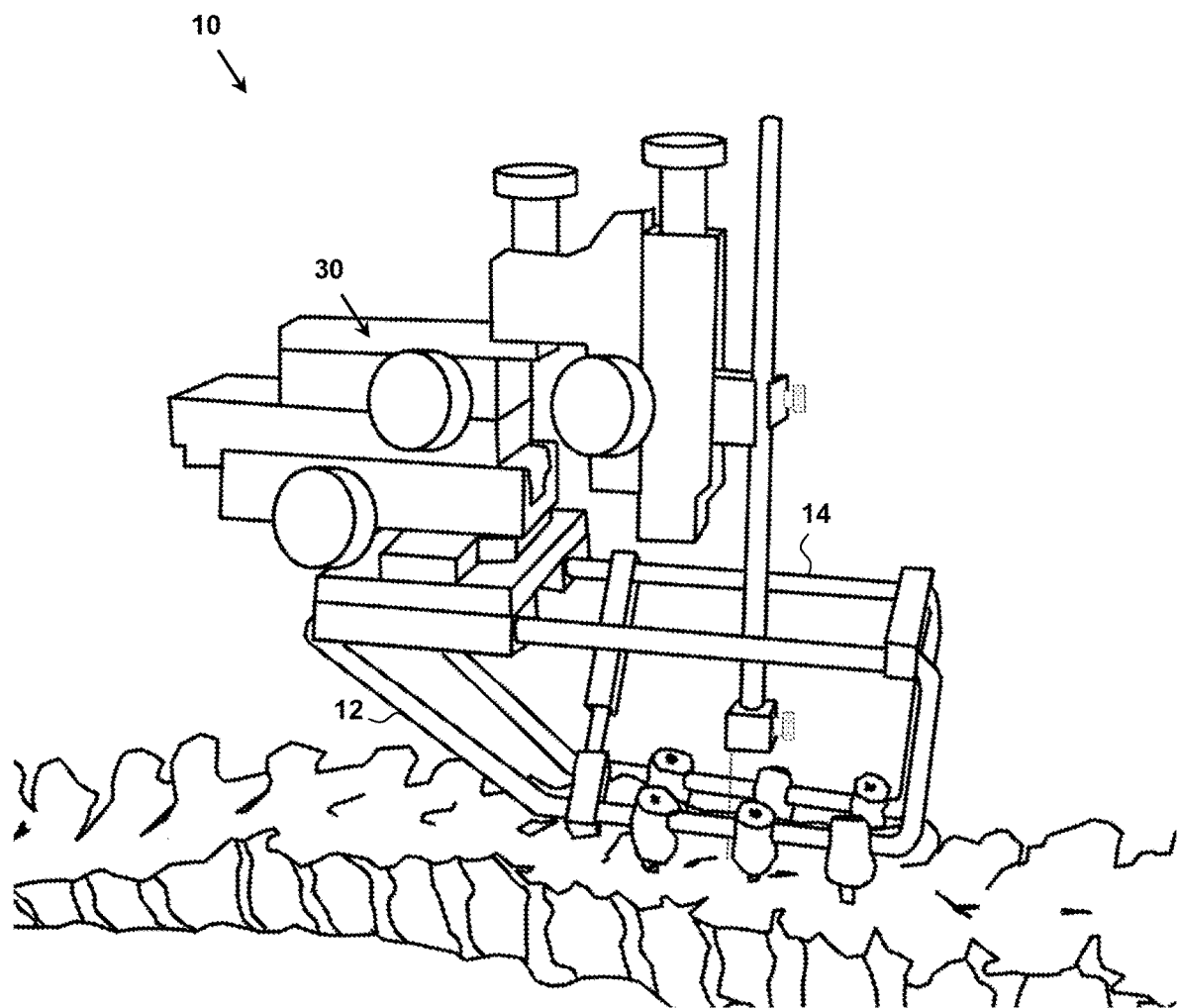
FIG. 10 is a perspective view of another embodiment of a system of the present invention in combination with a micromanipulator system holding an electrode mounted thereon, when the system is mounted on a human spine model.
Figure 11:
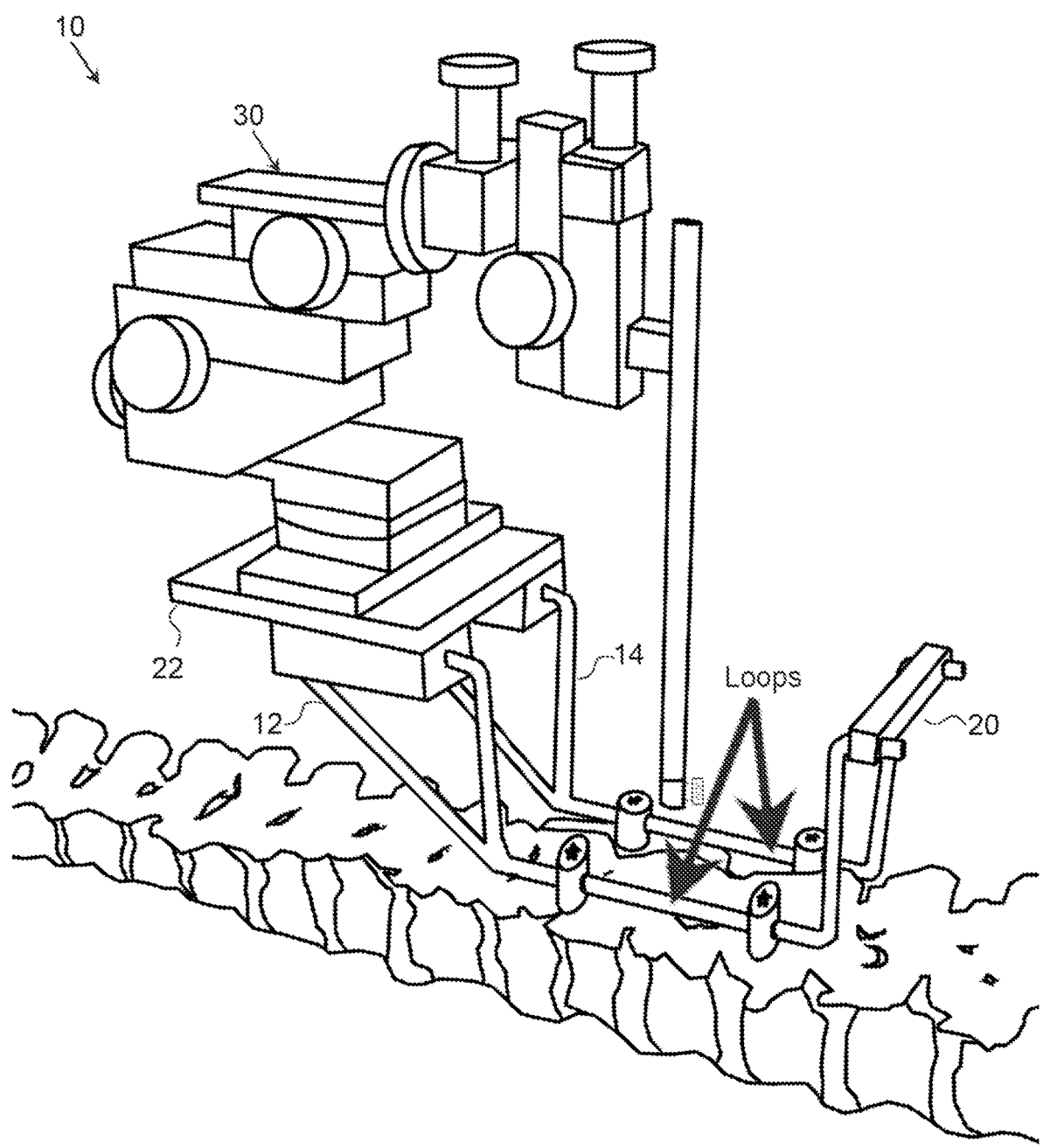
FIG. 11 is a perspective view of another embodiment of a system of the present invention in combination with a micromanipulator system holding an electrode mounted thereon, when the system is mounted on a human spine model.

As shown in FIG. 10, another embodiment of the frame (12, 14) is formed by a single surgical spine rod that is shaped under high heat to form a loop, with the terminal ends of the rod spot-welded together to close the loop.

As shown in FIGS. 11 to 15, another embodiment of the frame (12, 14) is formed by a single surgical spine rod that is shaped under high heat to form a frame comprising a vertically extending U-shaped portion. The trough of the U-shaped portion includes the lower part of the frame. In comparison to the closed loop configuration, the U-shaped portion allows for a wider working area in the transverse direction for ultrasound transducer maneuvers. At the upper end of one of the vertical legs of the U-shaped portion, the rod extends horizontally to form the upper part of the frame to which the platform (22) is attached. The rod then extends at an oblique angle back towards the trough of the U-shaped portion, and is spot welded thereto, to brace the upper part of the frame. At the upper end of the other one of the vertical legs of the U-shaped portion, the rod extends horizontally to allow for attachment of a c extending crosslink (20) between the frames (12, 14). In comparison with the embodiments shown in FIGS. 1 to 10, the embodiment of the frames (12, 14) shown in FIGS. 11 to 15 allows for an increase in the length of the upper part of the frames (12, 14) to which the platform is slidably attached, and thus an increase in the working range of the device mounted on the platform, without having to increase the required size of the surgical opening. Further, in contrast to the embodiments shown in FIGS. 1 to 9, it will be noted that in the embodiments shown in FIGS. 11 to 15, the upper part and lower part of each frame are longitudinally spaced apart from each other, such that they do not intersect a common vertically oriented plane extending in the transverse direction. This allows for a wider and more open working area above the surgical exposure in the transverse direction, without compromising stability. This wider and more open working area may be advantageous where the system includes an ultrasound probe (as discussed below) for guided imaging of the device, or needs to accommodate other tools that benefit from freedom of movement or unhindered line of sight between the frames.

Figure 15:
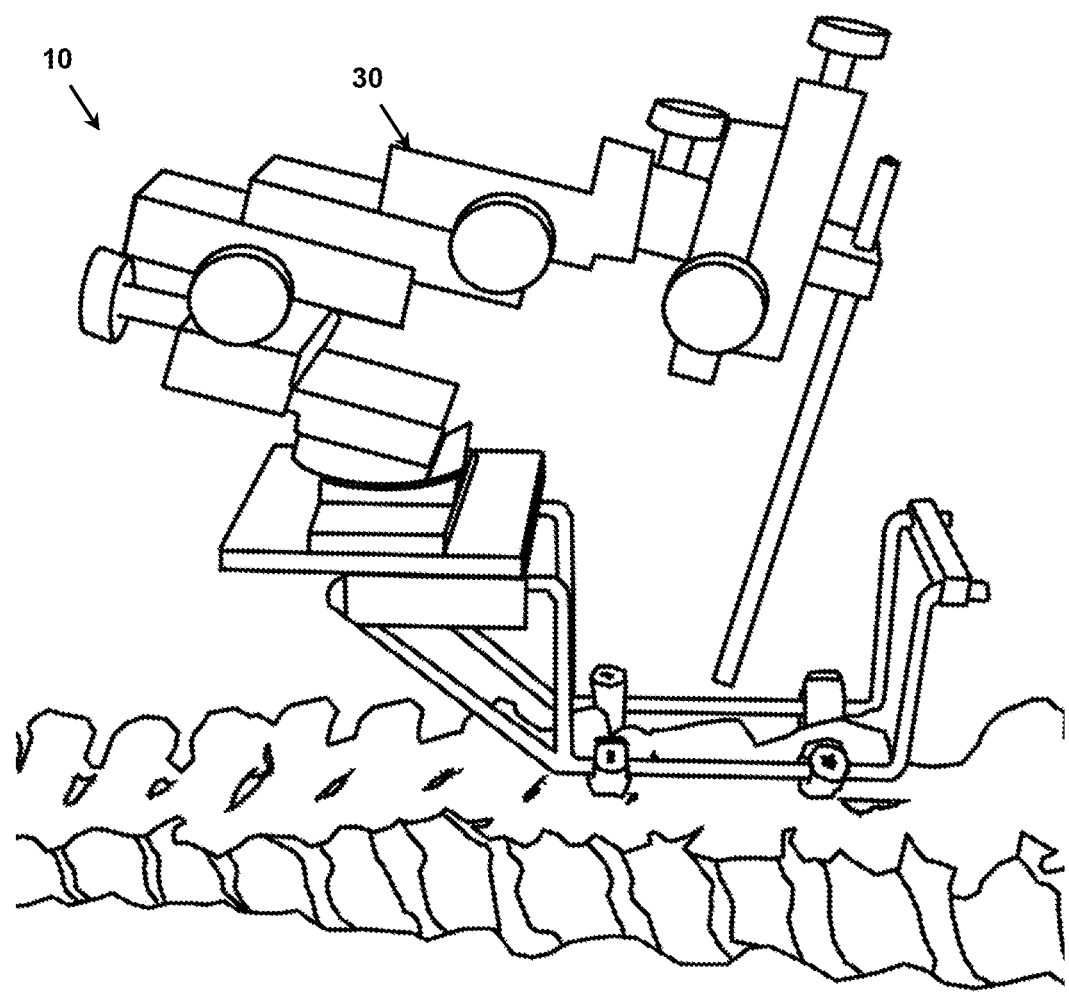
FIG. 15 is a side view of the system shown in FIG. 11, with the micromanipulator system holding the electrode rotated relative to the platform in the sagittal plane.
Figure 16:
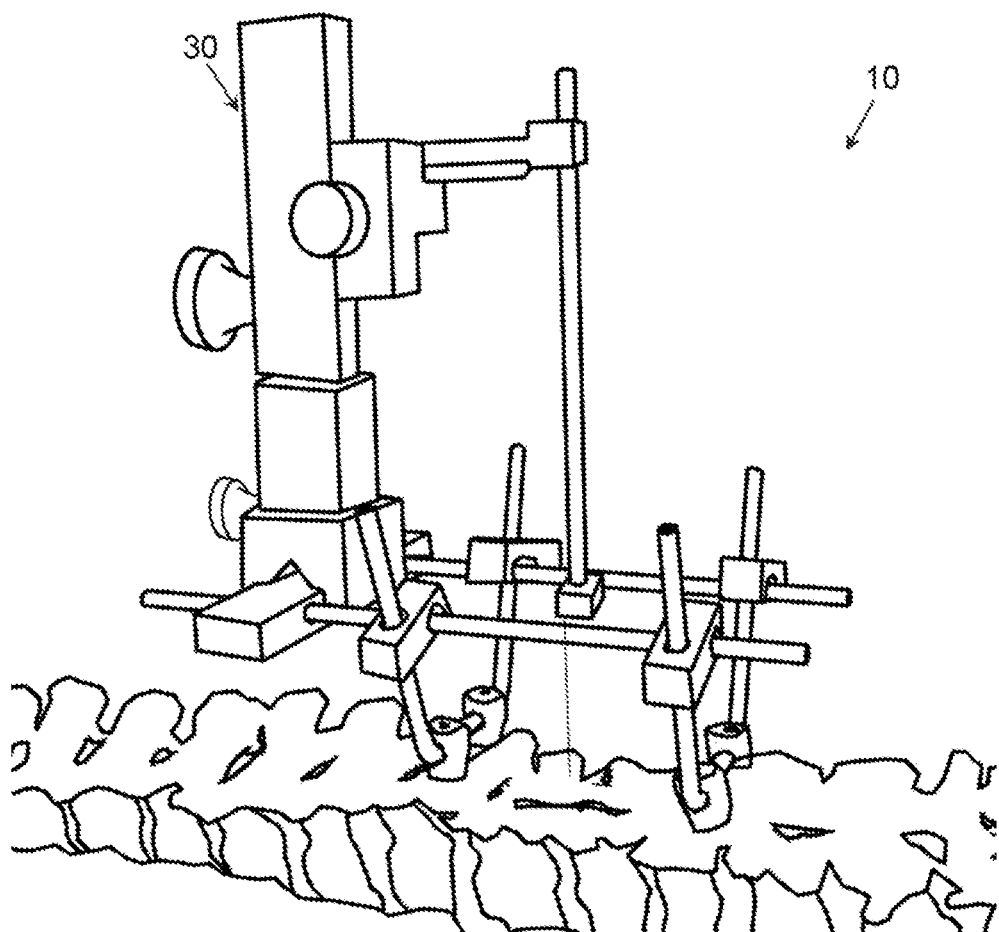
FIG. 16 is a perspective view of another embodiment of a system of the present invention in combination with a micromanipulator system holding an electrode mounted thereon, when the system is mounted on a human spine model.

As shown in FIG. 16, another embodiment of the frame is formed by rods shaped in to U-shape or V-shape posts in the transverse plane. Four connectors are used to slidably and pivotally connect the frames to two longitudinally extending rails, to which the platform is in turn attached. This transverse arrangement of frames may avoid interfering with the surgical site, where there is insufficient space along the surgical opening to accommodate the frames. On the other hand, the transverse arrangement of the frames means that the longitudinal distance between the points of fixation of the frames to the spine may be quite large compared to the embodiments shown in FIGS. 1 to 15. Thus, the embodiments of the frames shown in FIGS. 1 to 15 may be advantageous in providing a greater degree of fixation of spine, without compromising the size of the surgical window. Further, the embodiment shown in FIG. 16 has a greater number of parts (i.e., two frames, two rails, and four connectors). In contrast, the embodiments of the frames shown in FIGS. 1 to 15 allow for a minimalistic system with fewer parts. This simplicity, and the interlinked relationship of the parts, may allow for time savings and greater convenience in mounting of the system on the spine, as well as in manipulating and adjusting the system.

Pedicle screws. A purpose of the first and second pedicle screws (16, 18) is to fixedly attach the first and second frames (12, 14), respectively, to the spine. (Pedicle screws (16, 18) are known to persons skilled in the art of spinal surgery, as specialized bone screws that are normally used to hold rods in place along the spine in various surgeries such as spinal fixation, fusion or alignment surgeries.) Preferably, more than one pedicle screw (16, 18) is provided to attach each of the frames (12, 14) to more than one vertebrae of the spine, with one pedicle screw (16, 18), per frame, per vertebrae.

In the embodiment shown in the Figures, the pedicle screws (16, 18) are slidably attached to the associated frame to allow for selective adjustment of a horizontal position of the pedicle screw relative to the attached frame. Further, the pedicle screws (16, 18) are pivotally attached to the associated frame to allow for selective adjustment of an orientation of the pedicle screw relative to the attached frame. This sliding and pivotal attachment of the pedicle screws (16, 18) to the frame allows the pedicle screw to be properly positioned and oriented for screwing into different vertebrae having different morphologies. In the embodiment shown in the Figures, this sliding and pivotal attachment of the pedicle screws (16, 18) to the attached frame (12, 14) is achieved with the use of pedicle screw caps attached to the pedicle screws (16, 18). Each of these caps defines an aperture that receives a surgical spine rod that forms the frame (as discussed above), and allows for swiveling of the cap about the surgical spine rod. The pedicle screw caps can be tightened to fix their position and orientation relative to the frame (12, 16). Suitable examples of pedicle screw caps are commercially available (e.g., from Medtronic PLC, Dublin, Ireland).

Platform. A purpose of the platform (22) is to provide a base for mounting of a micromanipulator or another tool that holds the device, or the device itself. The platform (22) is attached to the upper parts of the first and second frames (12, 14) so as to be supported by the frames (12, 14) above the spine when the frames (12, 14) are fixedly attached by the pedicle screws (16, 18) to the spine.

As shown in FIGS. 1 to 10, in embodiments where the frames (12, 14) define closed loops, the platform (22) can be mounted anywhere along the top of the loops.

Figure 12:
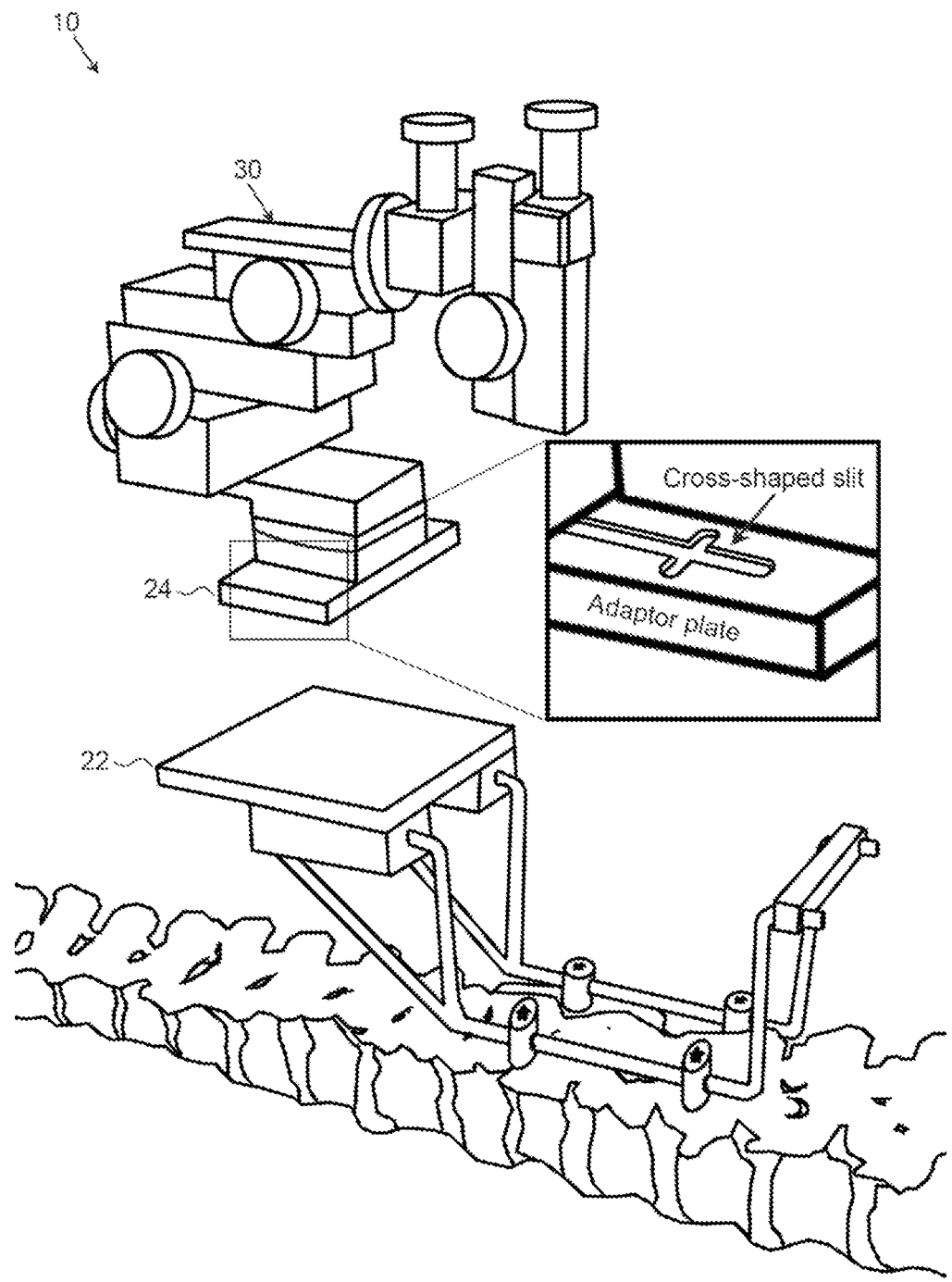
FIG. 12 is a perspective view of the system shown in FIG. 11, with the micromanipulator system removed to reveal the platform, and an enlarged view of the adaptor plate for attaching the micromanipulator system to the platform.
Figure 13:
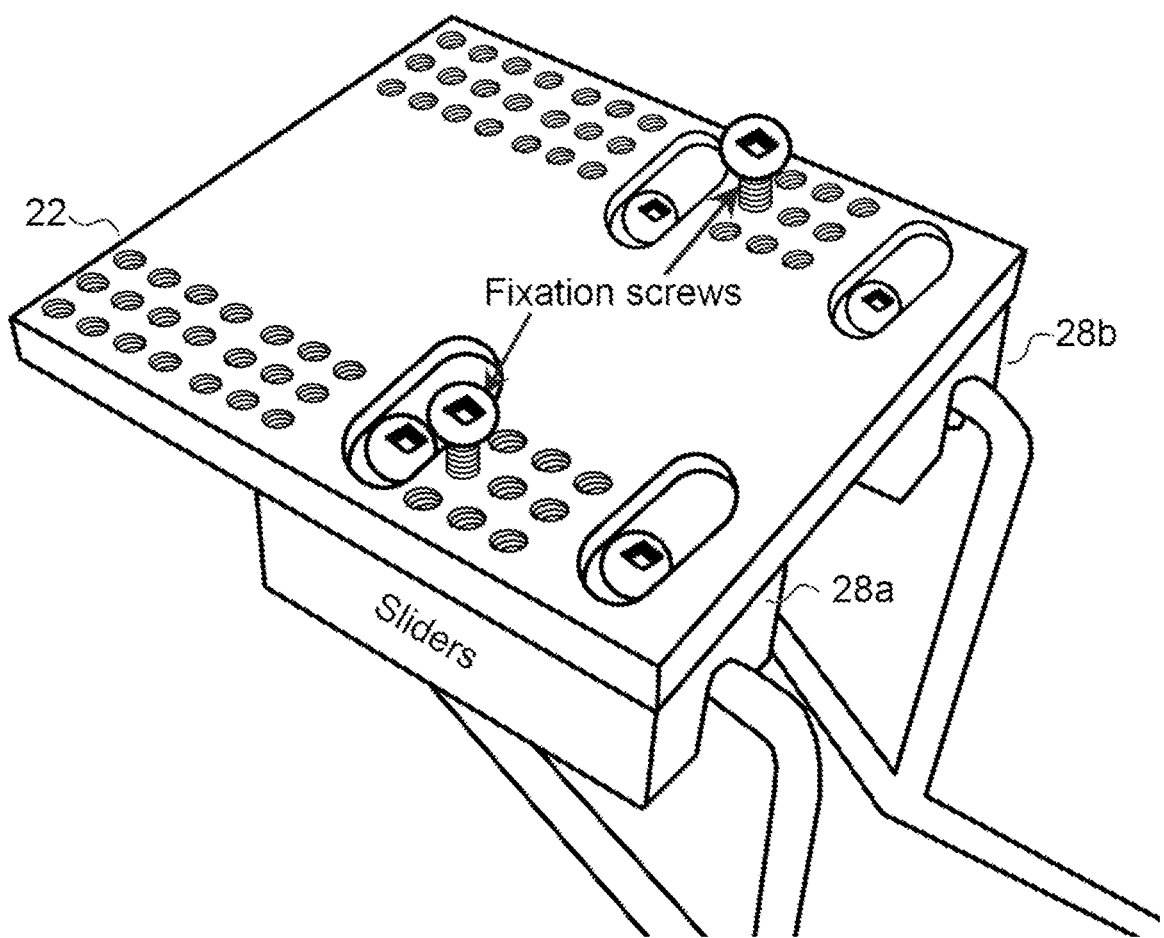
FIG. 13 is an enlarged perspective view of the platform assembly of the system shown in FIG. 11.

As shown in FIGS. 11 to 15, an embodiment of the platform (22) is adapted for mounting of a micromanipulator system to the frames (12, 14) for use in ISMS. The platform (22) is mounted to the cranial end of the loops, in order to maximize the working window distal to the platform (22) (typically about 11 cm). Referring to FIG. 12, the embodiment of the platform (22) is formed from a plate having a rectangular planar shape. As a non-limiting illustrative example, the plate has dimensions of about 8.5 cm in the longitudinal direction, and about 8 cm in the transverse direction. The micromanipulator system has an attached adaptor plate (24) defining a cross-shaped opening that receives the two fixation screws projecting upwardly from the platform (22). This allows the micromanipulator system to slide relative to the platform (22) in the longitudinal and transverse directions, and to be rotated in the coronal plane, so that the micromanipulator system can be selectively positioned on the platform (22). Referring to FIG. 13, the embodiment of the platform (22) is provided with an array of sixty screw holes arranged in ten rows in the longitudinal direction of the platform (22) and six columns in the transverse direction of the platform (22). The two fixation screws may be screwed into two of the sixty screw holes to provide for greater flexibility in the positioning of the adaptor plate (24) on the platform (22). Once the micromanipulator is in the desired position, the two fixation screws are tightened to fixedly secure the adaptor plate (24) to the platform (22).

The platform (22) is also slidably attached to the upper parts of the first and second frames (12, 14), to allow for selective adjustment of a longitudinal position of the platform (22) relative to the frame. Further, the platform (22) is also pivotally attached to the upper parts of the first and second frames (12, 14), to allow for selective adjustment of a horizontal distance between the lower part of the first frame (12) and the lower part of the second frame (14), while maintaining a horizontal orientation of the platform (22). This allows the frames (12, 14) to accommodate spines having different morphologies. Referring to FIG. 13, in an embodiment, the sliding and pivoting attachment of the platform (22) to the frames (12, 14) is achieved by attaching sliders (28) to the bottom side of the platform (22). As a non-limiting illustrative example, the slider may be about 5 cm long in the longitudinal direction. The bottom surface of each slider defines a groove that receives the surgical spine rod forming one of the frames (12, 14), and allows the frames (12, 14) to rotate in the transverse plane. For each slider, two transverse screws with cone tips are tightened to clamp the sliders (28) onto the frames (12, 14) This allows the platform to be easily detached and attached.

Figure 14:
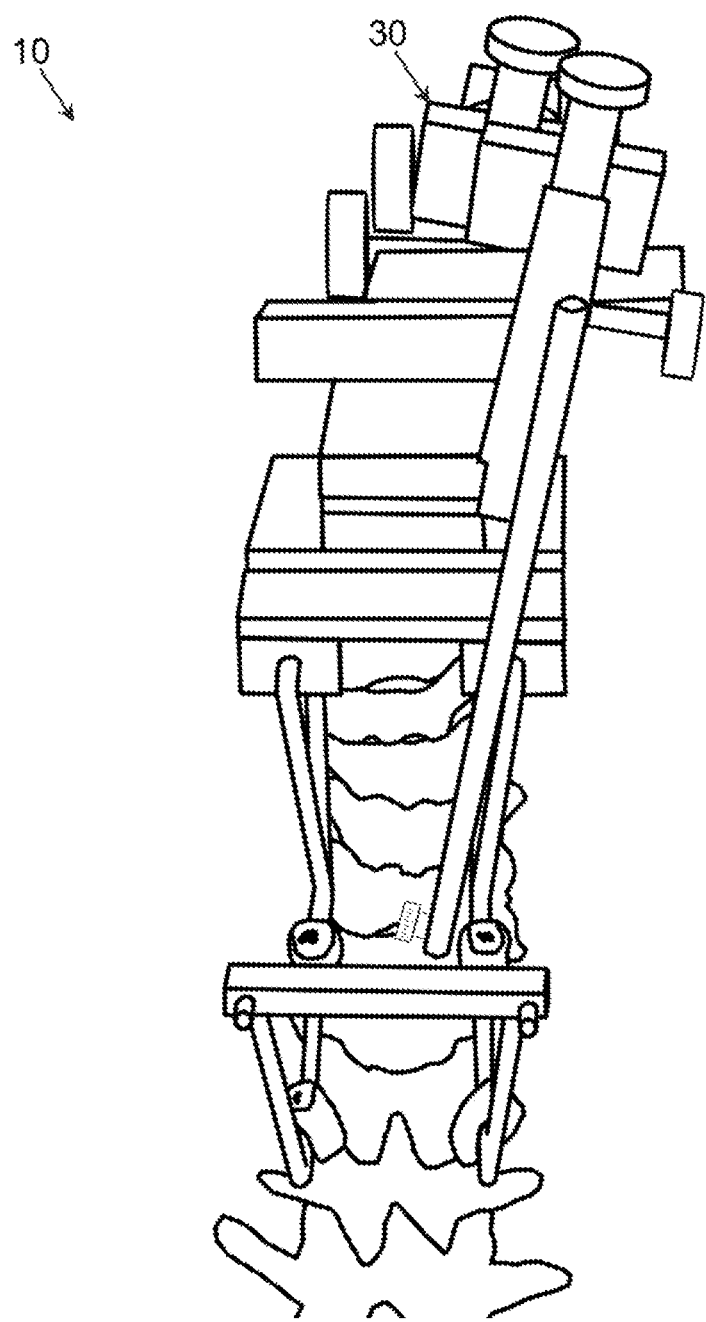
FIG. 14 is a caudal view of the system shown in FIG. 11, with the micromanipulator system holding the electrode rotated relative to the platform in the transverse plane.

Micromanipulator system. In an embodiment of the system (10) shown in FIG. 9, the system (10) includes a micromanipulator system (30) for holding the device, wherein the micromanipulator system (30) is mounted on the platform (22). In embodiments, the micromanipulator system (30) may be moveably mounted on the platform (22) for moving relative to the platform (22) in up to six degrees of freedom—that is, three directions of translation, rotation in the coronal plane, rotation in the transverse plane, and rotation in the sagittal plane. Suitable micromanipulator systems (30) are commercially available. A non-limiting illustrative example of such a micromanipulator system (30) is the MMN-33™ micromanipulator (Narishige Company, Tokyo, Japan) with ranges of movement of 35 mm craniocaudally, 20 mm mediolaterally, and 37 mm dorsoventrally. The MMN-33™ micromanipulator has a rotation mechanism that allows rotation in the transverse plane (as shown in FIG. 14). The Narishige micromanipulator is mounted on a 2D translation middle stage which allows for ranges of movement of an additional 60 mm in both the craniocaudal and mediolateral directions. The 2D stage is made of two single axis rack and pinion stages (Edmund Optics Inc, Barrington, N.J., USA). The bottom stage is a goniometer (B54-40U2NR, Suriga Seiki Company, Tokyo, Japan) which provides ±20 degrees of rotation in the sagittal plane (as shown in FIG. 15).

Figure 18:
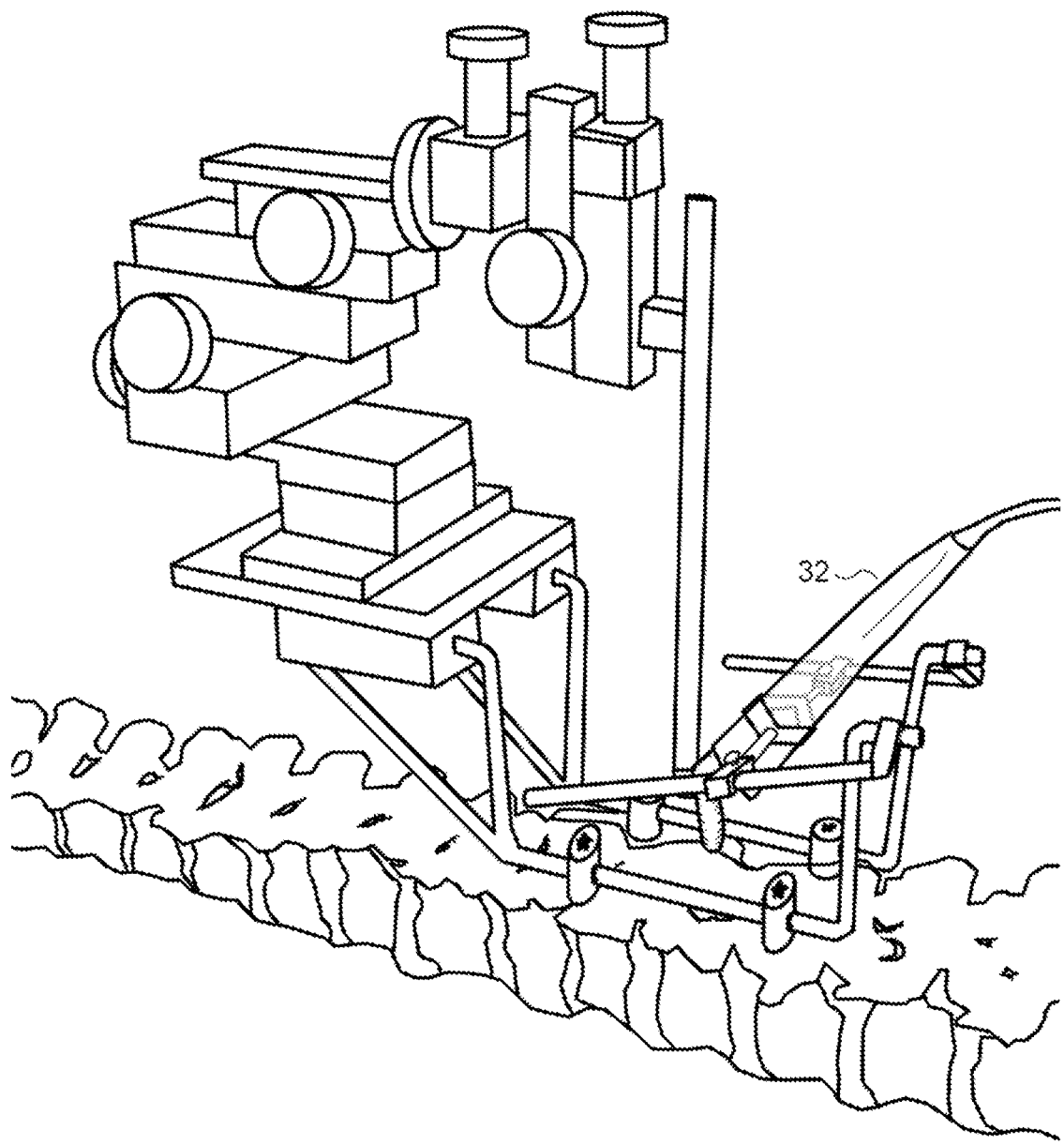
FIG. 18 is a perspective view of the system shown in FIG. 11 with the micromanipulator system holding a glass tube insertion tool instead of an electrode, when the system is mounted on the spine of a domestic pig.

Ultrasound probe. As shown in FIG. 18, in an embodiment of the system, the system includes an ultrasound probe (32) for use in dynamic, real-time imaging of the device. The ultrasound probe (32) may be hand held attached to the frame (12, 14). The ultrasound probe (32) may be pivotally attached to the frame to allow for selective adjustment of an orientation of the ultrasound probe (32) relative to the frame about a horizontally extending axis. Preferably, for ISMS, the ultrasound probe (32) is sized to fit in the space above the spinal cord and scan it in the transverse plane during electrode insertion. Suitable ultrasound probes (32) are commercially available. As a non-limiting illustrative example, the ultrasound probe (32) is an intraoperative L15-7io™ linear array probe with a footprint of 23 mm (Koninklijke Philips N.V.), with an operating frequency of the transducer set to 15 MHz. If the ultrasound probe (32) is not in contact with the spinal cord, it may be submerged in saline solution filling the spinal canal above the cord. Tilting the ultrasonic probe (32) to an angle of 25° to 45° in the transverse oblique scanning plane has been found to provide an acceptable contrast for viewing the gray and white matter of the spinal cord.

Mounting procedure. As shown in FIGS. 10 to 15, in exemplary use of embodiments of the apparatus for applications with a craniocaudal target window (i.e., long lengthwise along the spine), the frames (12, 14) are oriented to extend parallel with the spine in the longitudinal direction, with the frames (12, 14) placed on transversely opposite sides of the spine (i.e., on the left and right sides of the spine). Pedicle screws (16, 18) are placed bilaterally in the pedicles of two neighboring vertebrae, or two vertebrae skipping one level. The pedicle screw caps are attached to the pedicle screws (16, 18) and loosely secured to the frames (12, 14). One transverse crosslink (20) is loosely attached to connect the frames (12, 14) and provide some stability in the transverse direction. The platform (22) is loosely positioned on the frames (12, 14). The frames (12, 14) are then adjusted so that the midline of the platform (22) aligns with the spinal cord, and the platform (22) is parallel with the frontal plane of the body. The pedicle screw caps, crosslink(s) (20) and platform (22) screws are then securely tightened, locking all angles of the micromanipulator system (30). The micromanipulator system (30) is then placed on the platform (22) by sliding the adaptor plate (24) under the fixation screws of the platform (22). The micromanipulator system (30) is rotated on the platform (22) so that the main translation axis is aligned with the spinal cord (in the craniocaudal direction). The fixation screws of the platform (22) are fastened, locking the micromanipulator (30) in place.

As shown in FIG. 16, in another exemplary use of another embodiment of the system, the frames (12, 14) are oriented to extend transversely across the spine, with the frames (12, 14) spaced apart from each other in the longitudinal direction.

EXPERIMENTAL EXAMPLE NO. 1

Figure 17:
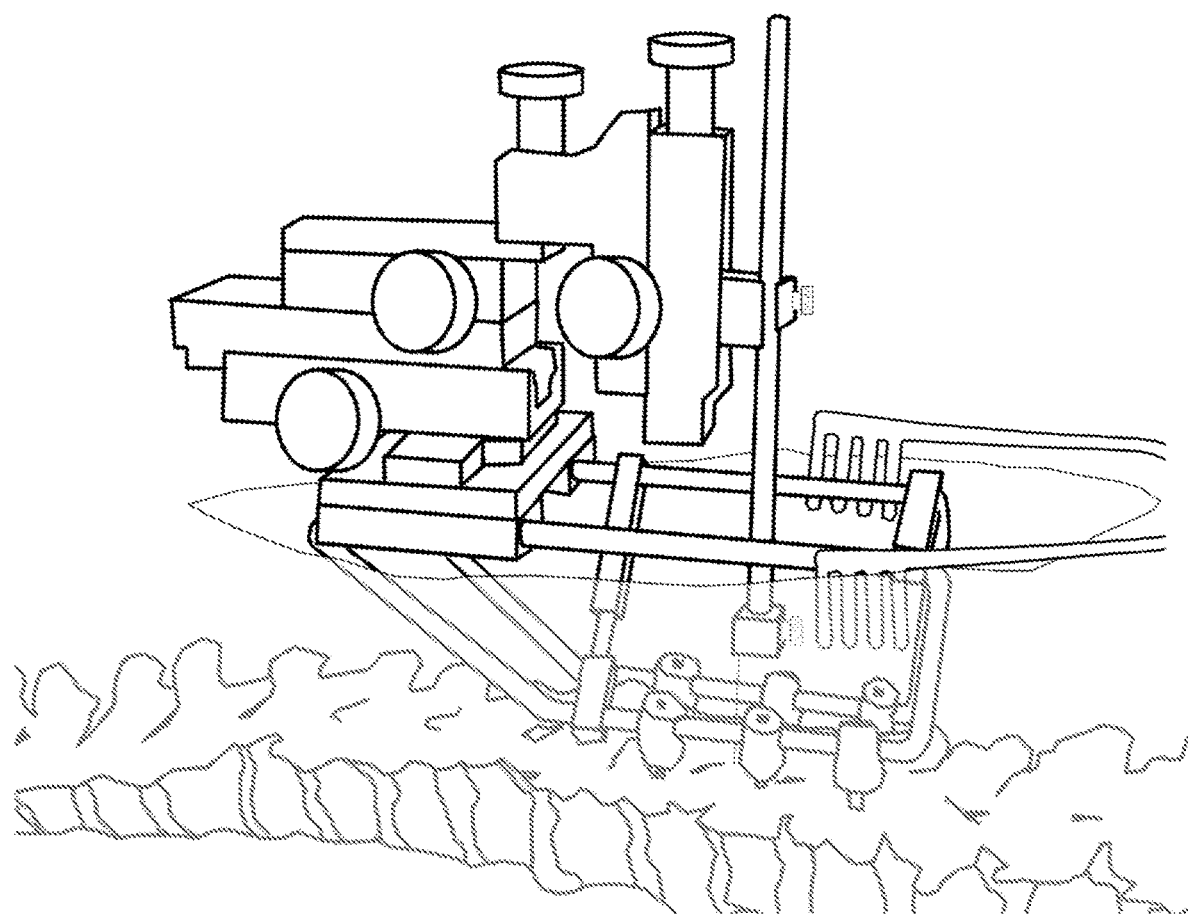
FIG. 17 is a perspective view of the system shown in FIG. 10, when the system is mounted on the spine of a domestic pig.

Referring to FIG. 17, the embodiment of the system shown in FIG. 10, was tested in a live pig experiment, for intraspinal microstimulation to produce hind limb movement. The pig is a good model for mechanical testing, as the spine and spinal cord are very similar in size to those of humans. The conclusions of the experiment were that: 1) The surgical procedure to mount the apparatus is very feasible for a surgeon who is experienced with spinal fixation procedures; 2) The frame mount to the vertebrae is very solid, even when only 4 pellicle screws are used; 3) The frame is mechanically very stable, even when only 1 horizontal and 1 diagonal crosslink are used; 4) The frame size and shape matched well with the bony anatomy of the pig (and hence human); 5) The frame provided a sufficiently large window to reach all targets in the spinal cord; 6) The spine fixation provided by the platform was sufficient to prevent spinal cord movement, even during extreme passive movements of the hind limbs which are known to cause movement of the spinal column and spinal cord.

EXPERIMENTAL EXAMPLE NO. 2

Figure 19:
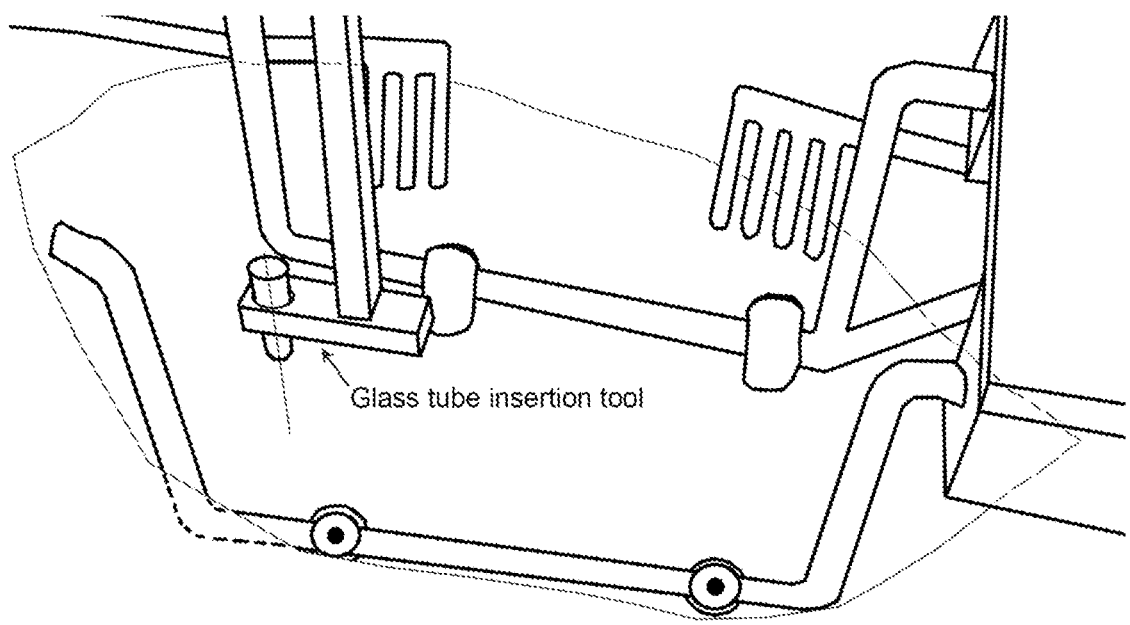
FIG. 19 shows an enlarged view of the glass tube insertion tool in the system of FIG. 18.

Ultrasound guided implantation of glass tube markers in the pig. The embodiment of the system shown in FIG. 11, was tested on domestic pigs. Intraoperative ultrasound imaging was used to guide the trajectory of glass-tube markers into the spinal cord prior to insertion. The glass-tube markers were approximately 5 mm long and had an outer diameter of 170 μm (Wale Apparatus Company, Hellertown, USA). The markers were inserted using a custom-built insertion tool, shown in FIG. 19, that replaces the electrode stylus in the micromanipulator shown in FIG. 18. The tool contains a holder for a 25 gauge needle. Prior to each insertion, a glass tube is back-loaded into a needle which is then placed in the holder. The needle is lowered by the micromanipulator and inserted in the spinal cord to 2 mm from the dorsal surface. The glass tube is then inserted through the needle in the spinal cord using a tungsten wire acting as a plunger. The needle is then carefully retracted with the micromanipulator, leaving the tube implanted in the cord.

Ultrasound visualization of electrode and spinal cord. In order to find the suitable tilt angle range of the ultrasound probe for viewing the gray and white matter of the spinal cord, a custom-made apparatus was used. The orientation of the probe was varied in the transverse oblique scanning plane to obtain the best gray and white matter contrast in cross-sectional images of the spinal cord. The suitable range in probe tilt angle (in the transverse oblique scanning plane) for visualizing the gray and white matter was found to be 25° to 45° from the short-axis view of the spinal cord. Tilt angles less than 25° did not provide sufficient contrast between gray and white matter to distinguish between them. While tilting the probe in the transverse oblique plane improves gray-white discrimination, it distorts the shape of the spinal cord in the dorsoventral direction. Therefore, the smallest tilt angle providing the appropriate contrast is preferred. When visualizing the electrode and the spinal cord in one image, the ultrasound probe was positioned caudal to the electrode in the transverse oblique plane.

Electrode alignment in the transverse plane. Traditionally for ISMS, surface landmarks such as dorsal root entry zone are used as reference points to determine the laterality of the entry point of the electrode. Since ultrasound imaging can visualize the gray and white matter, it can also be used to guide and provide feedback on the laterality of the entry point of the electrodes. Successful projections from the entry point to the target in the ventral horn require that the electrode is inserted "straight" into the spinal cord. For this purpose, "straight" is defined as perpendicular to the major axis of the cord's elliptical shape. In the case of a perfectly symmetrical cord, this would mean the electrode is also perpendicular to the line connecting the tips of the ventral or dorsal horns, and parallel with the anterior fissure. Therefore, the goal in the experiments was to align the marker insertion needle perpendicularly to cord's major axis, prior to insertion of the markers.

The angle of the insertion needle in the micromanipulator system was aligned using three methods: 1) eyeballing; 2) ultrasound guided while having the probe held by hand; and 3) ultrasound guided with the probe attached to the stereotactic setup. The probe was attached to the loops using a multi-jointed arm. These methods were investigated under two conditions: 1) no time limitation for insertion of each marker and in case of eyeballing no limitation on the points of view used by the surgeon (further referred to as unlimited time condition); and 2) time limit of 90 seconds for each insertion and for the eyeballing method and the surgeon was asked to remain along the side of the subject, thus limiting the viewpoints to a more realistic condition (further referred to as time constrained condition). Conditions 1 and 2 were each tested in 3 pigs. Prior to each of the insertion trials the initial alignment of the electrode was randomly set. In each experiment, at least 9 markers were implanted with each of the three alignment methods.

The ultrasound guided alignment of the insertion needle involved three steps: 1) Tilting the probe to visualize the electrode and the spinal cord in one image; 2) Identifying the orientation of the spinal cord by drawing a line (either in software or physically on a transparency sheet over the monitor) over the anterior fissure and/or drawing a line across the boundaries of the ventral or dorsal horns and/or, when the cord is oval-shaped, drawing a tangent line over the dorsal surface of the spinal cord at the midline; and 3) Adjusting the orientation of the electrode by rotating the micromanipulator in the transverse plane until the alignment becomes acceptable. Then, the micromanipulator rotation stage was locked and an ultrasound picture was taken of the needle in its final position prior to implantation. The insertion angle in this position was also documented. The marker was then implanted in the cord, as described above. Tilting the ultrasound probe in the transverse oblique plane did not affect the viewed orientation of the cross-section of the spinal cord.

Figure 20A:
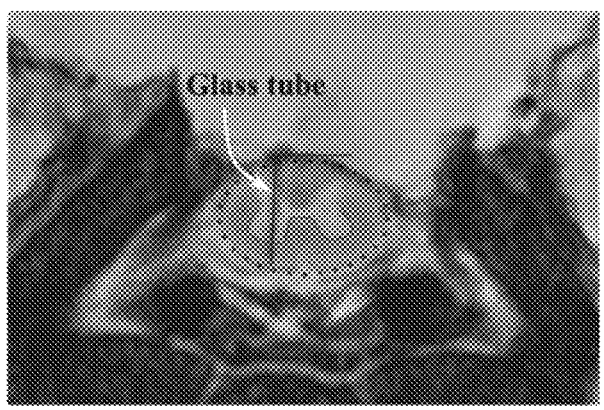
FIG. 20A shows an MR image of the spinal cord showing measurement of insertion angle of a glass tube.
Figure 20B:
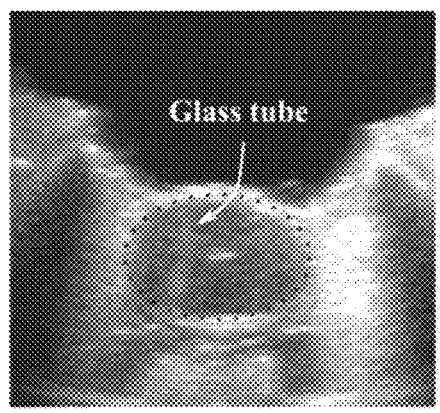
FIG. 20B shows ultrasound image (acquired using an embodiment of a system of the present invention) for a similar section of the spinal cord as shown in FIG. 20A.
Figure 20C:
FIG. 20C shows an MR image of the spinal cord in the transverse plane showing the gray and white matter.
Figure 20D:
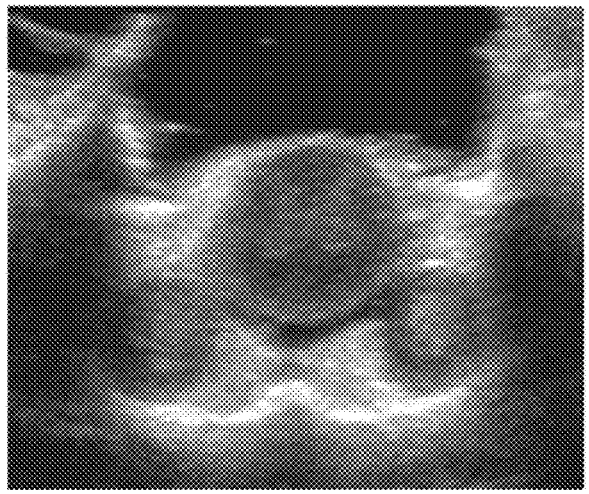
FIG. 20D shows an ultrasound image (acquired using an embodiment of a system of the present invention) of the transverse plane of the spinal cord for a similar section of the spinal cord as shown in FIG. 20C.

Electrode alignment in the sagittal plane. The space was not sufficient for ultrasound imaging of the insertion in the sagittal plane due to the design of the glass marker insertion tool. Therefore, an assisted eyeballing alignment method was used in the sagittal plane for all of the tested conditions. This method involved attaching a stylus to the micromanipulator and lowering it down to the dorsal surface of the spinal cord. The stylus was then translated in the craniocaudal direction while adjusting the sagittal rotation angle until its translation path became parallel with the surface of the spinal cord. In two experiments, after the markers were implanted into the spinal cord, the marker insertion tool was removed and an ultrasound image of the marker in the sagittal plane of the spinal cord was recorded and the insertion angle was documented (see FIGS. 20B and 20D).

Verification of marker placement using magnetic resonance imaging. After all of the markers were inserted into the spinal cord, the animal was euthanized (in case of the live pig experiment) and the lumbar spine (including the spinal cord) was extracted and fixed in formalin solution. The extracted spine was then scanned while submerged in saline using a 3T Siemens Prima™ MRI scanner at the Peter S. Allen MR Research Centre, University of Alberta. The MRI protocol used for these scans was a 3D MEDIC with a resolution of 0.25×0.25×1 mm in the transverse plane and 0.31×0.31×1 mm in the sagittal plane. The implanted markers in the spinal cord were tracked in the MR images and angle measurements were obtained using ImageJ™ software (U.S. National Institute of Health, Bethesda, Md., USA) (see FIGS. 20A and 20C). MR images were used as the reference for measurement of the insertion angles of the implanted markers with respect to (the major axis of) the spinal cord. Targeting errors of the ultrasound-guided implantation with the stereotactic system was calculated by comparison between the insertion angles measured using ultrasound imaging and MRI, before and after implantation.

Statistical analysis. A two-way ANOVA analysis was performed to compare the interaction between the testing conditions (time constrained condition and unlimited time condition) and the alignment methods (eyeballing, ultrasound guided using a handheld probe and ultrasound guided using a mounted probe) on the measured error in alignment of the electrode trajectory. For each of the testing conditions, comparisons between the errors resulting from the 3 alignment techniques were performed using one-way ANOVA and Tukey HSD post-hoc analysis. Similarly, for each of the alignment methods used, comparisons were made between the alignment errors obtained under the two testing conditions using paired t-tests. Differences were considered to be significant for $p \leq 0.05$. All analyses were performed using IBM SPSS™ software (version 22, IBM Co., Armonk, USA).

Assessment of detection accuracy. Detection accuracy of the electrode insertion angle was expressed as an error score defined by the difference between the marker insertion angle, measured from the MRI image, and the needle insertion angle, measured from the ultrasound image. In calculation of this error score, it was assumed that the marker insertion and careful tissue extraction steps (after the experiment), do not cause any changes in the alignment of the marker. The detection accuracy was measured for 137 insertions in 6 animals in the transverse plane and for 36 insertions in two animals in the sagittal plane. The detection accuracies were $2.15°\pm0.38°$ and $2.09°\pm0.35°$ (mean $\pm95\%$ confidence interval), in the transverse and sagittal planes respectively. Since the process of electrode alignment with the spinal cord in the stereotactic system is implemented in the spherical coordinate system, targeting error measurements are also conducted in this system.

Figure 4:
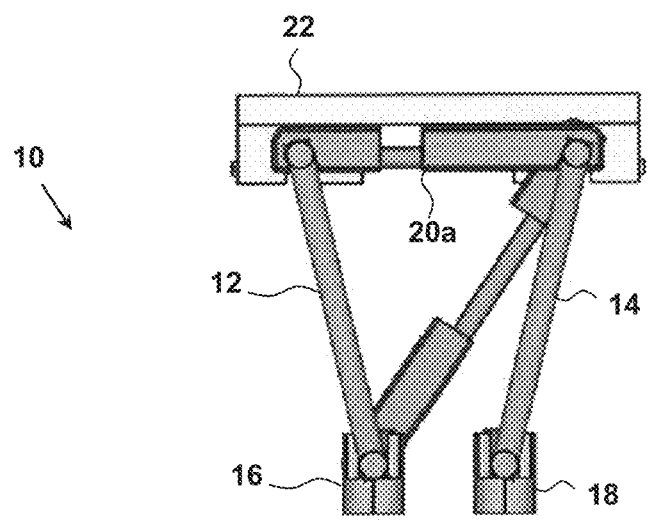
FIG. 4 is caudal view of the system shown in FIG. 1.

Assessment of alignment accuracy. Alignment accuracy of the electrode insertion was then expressed as the difference between the measured insertion angle on the MRI scans and the target electrode orientation, which is perpendicular to the major axis of the spinal cord (FIG. 4). Implementing the <0.5 mm acceptable spatial targeting error limit for ISMS, to the targeting error in the spherical coordinate system requires setting a targeting depth from the surface of the spinal cord. For ISMS, where locations within the ventral horns of the spinal cord are targeted, the targeting depth depends on the level and the size of the cord. The maximal depth of the ventral horns of the gray matter in the lumbar enlargement of the human spinal cord is approximately 6 mm from the dorsal surface. With this assumption, the 0.5 mm targeting error limit can be implemented by the following equations in the spherical coordinate system:

$$0.5 > \sqrt{r'^2 + (r)^2 - 2(r)r'[\sin(90°)\sin\theta'\cos(90° - \varphi') + \cos(90°)\cos\theta']} \quad (1)$$

where r is the depth of the target from the dorsal surface of the spinal cord, r' is the implanted length of the electrode, and $\varphi'$ and $\theta'$ are the electrode trajectory angles in the sagittal and transverse planes, respectively.

In 6 pig experiments, a total of 225 markers were implanted into the spinal cords using the assisted-eyeballing alignment method. The average sagittal plane alignment error was $1.4°\pm0.27°$ (mean $\pm95\%$ confidence interval). Considering equation 1, the ~1.5° error measured in the alignment technique used in the sagittal plane results in a limit of ~4.5° in the alignment error in the transverse plane.

Electrode alignment in the transverse plane was conducted under two conditions (time constrained and unlimited time) using three different techniques (eyeballing, ultrasound guidance using a handheld probe, and ultrasound guidance using a mounted probe). For both of the tested conditions, the deviation angle of the inserted electrodes using the ultrasound guided methods was significantly smaller than that for eyeballing ($p<0.01$ for unlimited time for both pairs, and $p<0.001$ for time constrained). However, deviation angles were not significantly different between the two ultrasound guided methods ($p=0.999$ for unlimited time, $p=0.841$ for time constrained). The upper bound for the confidence interval (95%) of the mean deviation angle for the ultrasound guided handheld probe method and ultrasound guided mounted probe were 2.45° and 2.63°, respectively for the unlimited time condition, and 3.07° and 3.57°, respectively for the time constrained condition.

The effect of limiting the insertion time and the view point for the eyeballing and ultrasound guided (only when probe fixed to the stereotactic setup) alignment methods was also found to be significant on the resulting deviation angle ($p=0.022$ and $p=0.020$, respectively). No statistically significant interaction was found between the condition (unlimited time, time constrained) and the alignment method ($p=0.21$).

Figure 21:
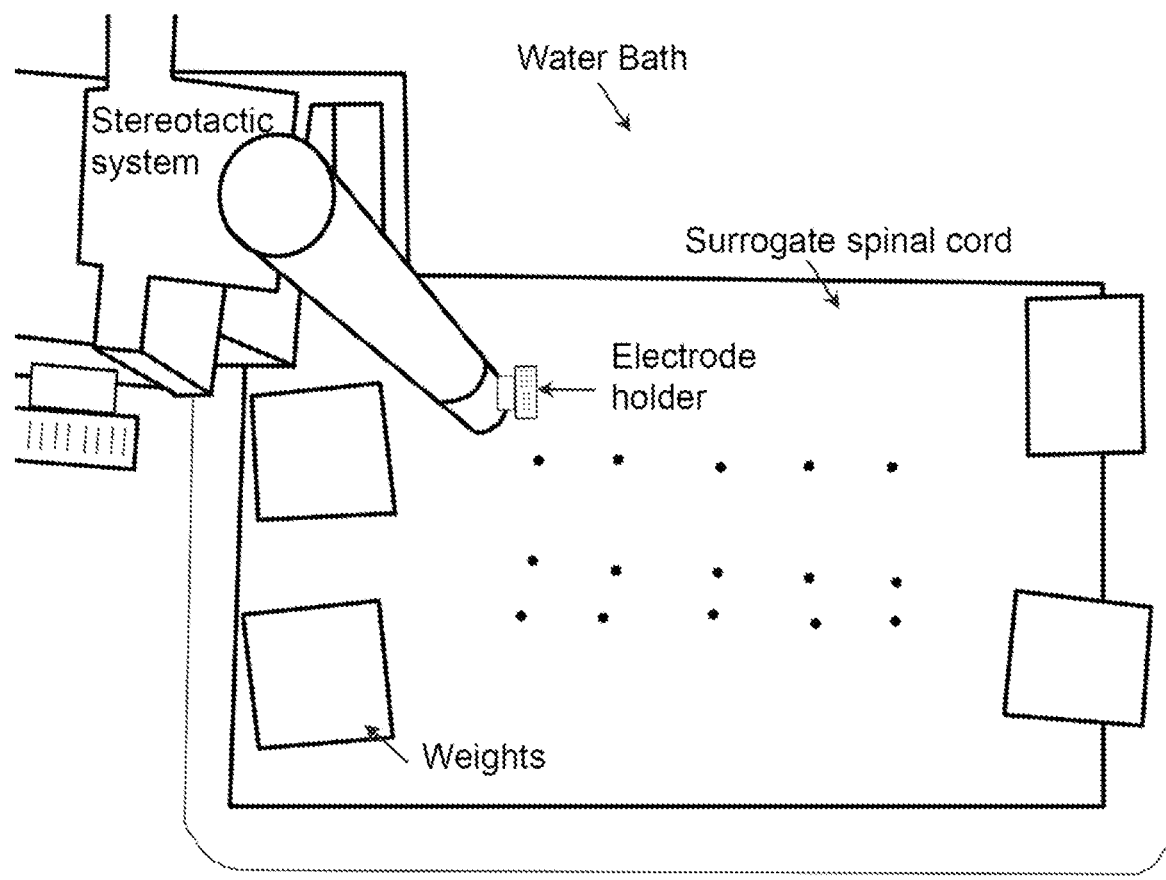
FIG. 21 shows a bench testing setup for experiments involving an embodiment of a system of the present invention on surrogate spinal cords made of hydrogel.

Experimental example no. 3—bench setup experiment on surrogate hydrogel spinal cords. Embodiments of the system of the present invention were subjected to bench setup experiments on surrogate gelatin hydrogel spinal cords, as shown in FIG. 21. Testing the ultrasound guided electrode implantation technique on the bench was aimed at assessing its capabilities and limitations in a more controlled setting with a higher spatial resolution. The bench setup and the testing protocol used not only directly measured the electrode insertion angle, but also allowed for reliable measurement of targeting depth in the transparent surrogate spinal cords. The bench setup used in this experiment can be utilized as a training tool for users of the proposed image guided stereotactic system. It can also provide a high throughput testing apparatus of the accuracy of targeting of various systems for intraspinal interventions.

Surrogate hydrogel spinal cords were used due to their transparency and near physiological mechanical properties. The surrogate spinal cords were 7 cm long and were made in molds with the cross-sectional size of the lumbar enlargement of feline spinal cords: ovals with a major diameter of 8 mm and a minor diameter of 6 mm. A cut was made at the midline of these spinal cords to simulate the anterior fissure. The anterior side of the spinal cords were fixed onto a plastic plate with 5 drops of cyanoacrylate glue. The dorsal surface of the spinal cords was painted black to blind the operator from using visual feedback for alignment. The plastic plate was then placed in a transparent container filled with saline. Weights were used to prevent the plastic plate and the spinal cord attached from floating. The spinal stereotactic setup was fixed over the container with the electrode holder positioned over the spinal cord.

A 125 μm diameter Pt/Ir electrode (FHC Company, Bowdoin, Me., USA) was used for insertion into the surrogate spinal cord. Alignment of the electrode prior to insertion was performed under the guidance of the ultrasound images (acquired with the probe held by hand) in both the transverse and sagittal planes. The alignment protocol used was the same as described above for experimental example no. 2. The landmarks used for identifying the alignment of the surrogate spinal cords in the ultrasound images were the orientation of the dorsal surface and the orientation of the simulated anterior fissure. Ultrasound images were taken for each insertion. Similar to the pig experiments, before each trial the initial orientation of the electrode was randomly set. After the electrode was aligned perpendicularly with respect to the spinal cord, the electrode was inserted to the depth of 4 mm using the micromanipulator. In order to mark the electrode track in the spinal cord for further analysis, electrical stimulation was used. Direct current (DC) stimulation at 20 V amplitude was delivered across the implanted electrode and a return needle electrode (placed in the saline bath). After the stimulation was turned on the electrode was slowly retracted from the spinal cord to mark the full length of the track. A camera was positioned parallel to the sagittal plane of the cord to measure the insertion angle in this plane. In each surrogate spinal cord three to five tracks were made from electrode insertions. After all insertions were completed and tracks marked, the surrogate spinal cords were detached from their underlying plate and thin transverse sections were cut, each containing one electrode track. Microscopic images were taken from these sections to measure the insertion angle and the track length in the transverse plane. All angle measurements in the microscopic images were obtained using the ImageJ™ software.

Assessment of detection accuracy. Detection accuracy of the electrode insertion angle in the benchtop experiments was expressed by the difference between the measured insertion angle based on the ultrasound image and the measured angle from the microscopy image of the surrogate spinal cord section. The detection accuracies were 1.98°±0.84° and 0.91°±0.31° (mean ±95% confidence interval), in the transverse and sagittal planes respectively.

The bench setup not only allowed the measurement of the alignment accuracy (deviation angles in transverse and sagittal planes as also measured in pigs), but also allowed the direct measurement of the spatial targeting error (3D distance from target which in addition to the alignment error also includes the error associated with the implantation depth). Alignment accuracy of the inserted electrodes in the sagittal and transverse planes were 0.95°±0.5° and 2.295°±0.81° (mean ±95% confidence interval), respectively. Depth of the electrode tips in the transverse plane was 3.95±0.11 mm. Based on these results, the spatial targeting error of ultrasound-guided implantation can be calculated using equation (1) above (in this case, r=4 mm), and was found to be 0.22±0.022 mm (mean±standard deviation). These results were obtained for a surrogate cat spinal cord and target depth of 4 mm for the electrode tip. Based on the measured deviation angles, if the targeting depth for the lumbar enlargement of a human spinal cord were to be considered (maximal gray matter depth of 6 mm), and assuming perfect depth targeting (r=r'=6 mm), the calculated spatial targeting error (equation 1) remains below the 0.5 mm limit. The upper boundary of the spatial targeting error in this case is calculated to be 0.32 mm, using the upper boundaries of the 95% confidence intervals of the measured deviation angles for the electrode trajectory.

Experimental example no. 4. In order to demonstrate the application of the ultrasound guided spinal stereotactic system for intraoperative ISMS, an experiment was conducted in a domestic pig (weight: 51 kg). A 100 µm Pt/Ir electrode was used (FHC Co., Bowdoin, Me., USA) and the stimulation trains consisted of: frequency of 50 Hz, pulse width of 200 µs, biphasic charge-balanced pulses with amplitudes up to 150 µA. A needle return electrode was placed in the paraspinal muscles. In order to visualize the movements generated by ISMS, the animal's legs were suspended. For kinematic analysis of the generated movements, black marks were painted on the hip, knee, ankle and metatarsophalangeal (MTP) joints as well as on the iliac crest, and videos of the generated movements were recorded. Electromyographic (EMG) signals were also recorded using a Noraxon™ digital telemetry system and ambu blue sensor electrodes (Noraxon Co., Scottsdale, Ariz., USA). Pairs of EMG electrodes were placed on the following muscles: rectus femoris, biceps femoris, lateral gastrocnemius and tibialis anterior. The kinematics and EMG data were analyzed using custom-written programs in Matlab™ (version 2015a, MathWorks Co., Natick, USA).

The lumbar enlargement of the spinal cord of a live pig was intraoperatively mapped using the ultrasound guided spinal stereotactic system. Functional organization of the mapped region of the spinal cord for producing leg movements in this animal was consistent with functional maps available for the lumbar spinal cords of pigs, cats and rhesus monkeys, in the rostrocaudal direction.

Although this study only focused on the application of intraoperative ISMS, the system has the potential to be used for implantation of ISMS arrays for chronic use as well. This may be realized by using a modified electrode holder design that can release the electrodes after implantation.

Definitions and Interpretation. References in the specification to "one embodiment", "an embodiment", etc., indicate that the embodiment described may include a particular aspect, feature, structure, or characteristic, but not every embodiment necessarily includes that aspect, feature, structure, or characteristic. Moreover, such phrases may, but do not necessarily, refer to the same embodiment referred to in other portions of the specification. Further, when a particular aspect, feature, structure, or characteristic is described in connection with an embodiment, it is within the knowledge of one skilled in the art to affect or connect such module, aspect, feature, structure, or characteristic with other embodiments, whether or not explicitly described. In other words, any module, element or feature may be combined with any other element or feature in different embodiments, unless there is an obvious or inherent incompatibility, or it is specifically excluded. It is further noted that the claims may be drafted to exclude any optional element. As such, this statement is intended to serve as antecedent basis for the use of exclusive terminology, such as "solely," "only," and the like, in connection with the recitation of claim elements or use of a "negative" limitation. The terms "preferably," "preferred," "prefer," "optionally," "may," and similar terms are used to indicate that an item, condition or step being referred to is an optional (not required) feature of the invention. The singular forms "a," "an," and "the" include the plural reference unless the context clearly dictates otherwise. The term "and/or" means any one of the items, any combination of the items, or all of the items with which this term is associated. The phrase "one or more" is readily understood by one of skill in the art, particularly when read in context of its usage. The term "about" can refer to a variation of ±5%, ±10%, ±20%, or ±25% of the value specified. For example, "about 50" percent can in some embodiments carry a variation from 45 to 55 percent. For integer ranges, the term "about" can include one or two integers greater than and/or less than a recited integer at each end of the range. Unless indicated otherwise herein, the term "about" is intended to include values and ranges proximate to the recited range that are equivalent in terms of the functionality of the composition, or the embodiment. As will be understood by one skilled in the art, for any and all purposes, particularly in terms of providing a written description, all ranges recited herein also encompass any and all possible sub-ranges and combinations of sub-ranges thereof, as well as the individual values making up the range, particularly integer values. A recited range includes each specific value, integer, decimal, or identity within the range. Any listed range can be easily recognized as sufficiently describing and enabling the same range being broken down into at least equal halves, thirds, quarters, fifths, or tenths. As a non-limiting example, each range discussed herein can be readily broken down into a lower third, middle third and upper third, etc. As will also be understood by one skilled in the art, all language such as "up to", "at least", "greater than", "less than", "more than", "or more", and the like, include the number recited and such terms refer to ranges that can be subsequently broken down into sub-ranges as discussed above. In the same manner, all ratios recited herein also include all sub-ratios falling within the broader ratio.

REFERENCES

1. Federici T, Hurtig C V, Burks K L, Riley J P, Krishna V, Miller B A, et al: Surgical Technique for Spinal Cord Delivery of Therapies: Demonstration of Procedure in Gottingen Minipigs. *J Vis Exp JoVE:*2012.
2. Riley J P, Raore B, Taub J S, Federici T, Boulis N M: Platform and cannula design improvements for spinal cord therapeutics delivery. *Neurosurgery* 69:ons147-154; discussion ons155, 2011).
3. Riley J, Federici T, Polak M, Kelly C, Glass J, Raore B, et al: Intraspinal stem cell transplantation in amyotrophic lateral sclerosis: a phase I safety trial, technical note, and lumbar safety outcomes. Neurosurgery 71:405-416; discussion 416, 2012.
4. Riley J, Butler J, Baker K B, McClelland S, Teng Q, Yang J, et al: Targeted spinal cord therapeutics delivery: stabilized platform and microelectrode recording guidance validation. Stereotact Funct Neurosurg 86:67-74, 2008.
5. Busscher I, Ploegmakers J J W, Verkerke G J, Veldhuizen A G: Comparative anatomical dimensions of the complete human and porcine spine. Eur Spine J 19:1104-1114, 2010.
6. Grahn P J, Goerss S J, Lujan J L, Mallory G W, Kall B A, Mendez A A, et al: MRI-Guided Stereotactic System for Delivery of Intraspinal Microstimulation. Spine 41:E806-813, 2016.

The invention claimed is:

1. A stereotactic system for positioning a device relative to a spine extending craniocaudally in a horizontal longitudinal direction, wherein the system comprises:
(a) a first frame comprising a lower part and an upper part, and at least one first pedicle screw attached to the first frame for fixedly attaching the lower part of the first frame to the spine;
(b) a second frame comprising a lower part and an upper part, and at least one second pedicle screw attached to the second frame for fixedly attaching the lower part of the second frame to the spine, wherein the lower part of the second frame is horizontally spaced apart from the lower part of the first frame; and
(c) a platform for mounting the device, wherein;
the platform is attached to the upper part of the first frame and the upper part of the second frame so as to be supported by the first and second frames above the spine when the first and second frames are fixedly attached by the at least one first and second pedicle screws to the spine;
(ii) the platform is slidably attached to the upper part of the first frame and the upper part of the second frame for changing a horizontal longitudinal position of the platform relative to the first and second frames; and
(iii) the platform is pivotally attached to the upper part of the first frame and to the upper part of the second frame such that pivoting of the first frame and the second frame relative to the platform changes a horizontal distance between the lower part of the first frame and the lower part of the second frame, while maintaining a constant orientation of the platform.

2. The system of claim 1, wherein the upper part and the lower part of the first frame intersect a common vertically oriented plane extending in a horizontal transverse direction substantially perpendicular to the horizontal longitudinal direction.

3. The system of claim 1, wherein the upper part and the lower part of the first frame are spaced apart in the horizontal longitudinal direction, such that the upper part and the lower part of the first frame do not intersect a common vertically oriented plane extending in a horizontal transverse direction substantially perpendicular to the horizontal longitudinal direction.

4. The system of claim 1, wherein the first frame defines a vertically extending closed loop formed in part by the upper part and the lower part of the first frame.

5. The system of claim 1, wherein the lower part of the first frame is formed by at least one elongate rod, and the at least one first pedicle screw comprises a plurality of first pedicle screws.

6. The system of claim 5, wherein the at least one elongate rod is a metallic surgical spine rod.

7. The system of claim 1, wherein the system further comprises at least one length-adjustable brace member attached to the first frame and the second frame.

8. The system of claim 1, wherein each of the at least one first pedicle screw is slidably attached to the first frame to allow for selective adjustment of a horizontal position of the at least one first pedicle screw relative to the first frame.

9. The system of claim 1, wherein each of the at least one first pedicle screw is pivotally attached to the first frame to allow for selective adjustment of an orientation of the at least one first pedicle screw relative to the first frame.

10. The system of claim 1, wherein the system comprises a micromanipulator for holding the device, wherein the micromanipulator is mounted on the platform.

11. The system of claim 10, wherein the micromanipulator may be moveably mounted on the platform.

12. The system of claim 1, wherein the system comprises an ultrasound probe for use in dynamic, real-time imaging of the device.

13. The system of claim 12, wherein the ultrasound probe is attached to the first frame.

14. The system of claim 13, wherein the ultrasound probe is pivotally attached to the first frame to allow for selective adjustment of an orientation of the ultrasound probe relative to the first frame about a horizontally extending axis.

15. The system of claim 1, wherein the platform is pivotally attached to the upper part of the first frame and to the upper part of the second frame such that pivoting of the first frame and the second frame relative to the platform changes the horizontal distance between the lower part of the first frame and the lower part of the second frame in a horizontal transverse direction substantially perpendicular to the horizontal longitudinal direction.

* * * * *

UNITED STATES PATENT AND TRADEMARK OFFICE
CERTIFICATE OF CORRECTION

PATENT NO. : 11,058,510 B2
APPLICATION NO. : 16/140203
DATED : July 13, 2021
INVENTOR(S) : Toossi et al.

It is certified that error appears in the above-identified patent and that said Letters Patent is hereby corrected as shown below:

In the Specification

Column 1, Line 3, directly underneath the title insert:
--This invention was made with government support under grant W81XWH-12-1-0335 awarded by the Department of Defense. The government has certain rights in the invention.--

Signed and Sealed this
Tenth Day of December, 2024

Katherine Kelly Vidal
*Director of the United States Patent and Trademark Office*